United States Patent [19]

Minagawa et al.

[11] 4,378,443

[45] Mar. 29, 1983

[54] 2,2,6,6-TETRAALKYL-4-PIPERIDYL-BIX-SPIRO-ETHERS AS LIGHT STABILIZERS FOR SYNTHETIC POLYMERS

[75] Inventors: Motonobu Minagawa, Koshigaya; Naohiro Kubota, Ageo; Toshihiro Shibata, Omiya, all of Japan

[73] Assignee: Adeka Argus Chemical Co., Ltd., Urawa, Japan

[21] Appl. No.: 195,578

[22] Filed: Oct. 8, 1980

[30] Foreign Application Priority Data

Oct. 11, 1979 [JP] Japan .................................. 54-131051

[51] Int. Cl.³ .................... C07D 491/113; C08K 5/34
[52] U.S. Cl. .................................. 524/102; 524/291; 524/343; 546/19
[58] Field of Search ................. 260/45.8 NZ; 546/19, 546/102

[56] References Cited

U.S. PATENT DOCUMENTS 4,105,626  8/1978  Brunetti et al. ................... 546/19
4,128,608  12/1978 Minagawa et al. ............... 524/102
4,212,974  7/1980  Murayama et al. .......... 260/45.8 NZ
4,222,931  9/1980  Minagawa et al. .......... 260/45.8 NZ
4,323,684  4/1982  Kubota et al. .................... 546/19

Primary Examiner—Lorenzo B. Hayes
Assistant Examiner—R. A. White

[57] ABSTRACT 2,2,6,6-Tetraalkyl-4-piperidyl-bis-spiro-ethers are provided, useful as stabilizers for lessening deterioration due to exposure to light of organic polymeric materials, and having the general formula:

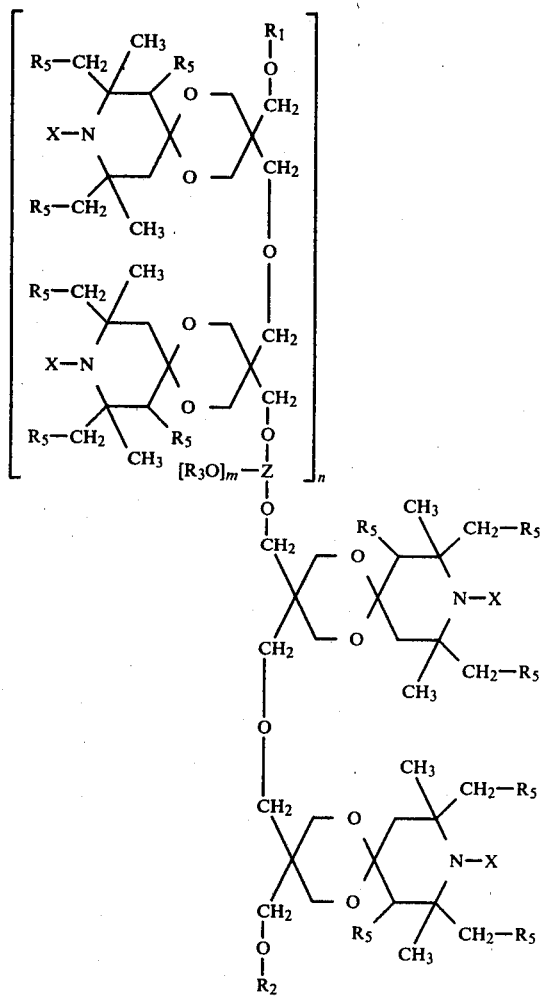

27 Claims, No Drawings

2,2,6,6-TETRAALKYL-4-PIPERIDYL-BIX-SPIRO-ETHERS AS LIGHT STABILIZERS FOR SYNTHETIC POLYMERS

Hindered 2,2,6,6-tetraalkyl-4-carboxylic acid ester piperidine compounds having been proposed by Murayama et al. U.S. Pat. No. 3,640,928, patented Feb. 8, 1972 as light and heat stabilizers for synthetic polymers, such as polyolefins, polyvinyl chloride, polyvinylidene chloride, polyurethanes, and polyamides. These compounds have the general formula:

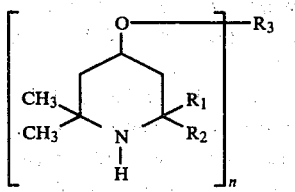

or a salt thereof.

In the above formula:

$R_1$ and $R_2$ which may be the same or different, each are an alkyl group such as methyl, ethyl, isopropyl or dodecyl, or they form, together with the carbon atom to which they are attached, a saturated alicyclic group such as:

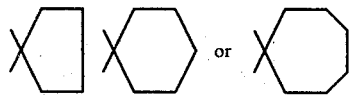

or a group of the formula

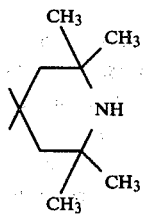

n is an integer of 1 to 3 inclusive; and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al. patent has been followed by a large number of patent and literature disclosures by Murayama et al. and others of compounds including a 2,2,6,6-tetrasubstituted-4-piperidyl group attached to a base molecule of varying structures.

Murayama et al. U.S. Pat. No. 3,898,303 patented Aug. 5, 1975 propose piperidino-spiro-hydantoin derivatives having the formula:

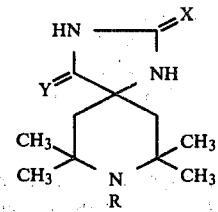

wherein: R represents an alkyl group, an alkenyl group, an alkenoyl group which may be substituted with an aryl group, a hydroxyalkyl group, an alkoxy-alkyl group, an alkoxycarbonylalkyl group, an acyloxyalkyl group, a cyanoalkyl group or nitroso group, and X and Y individually represent oxygen atom or sulfur atom.

Murayama et al. in U.S. Pat. No. 3,899,464 patented Aug. 12, 1975 discloses a variation of the piperidino spiro compounds having the formula:

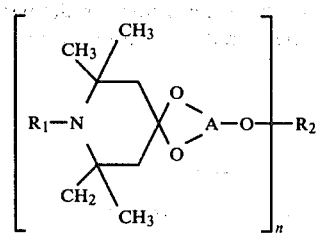

wherein:

$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4;

when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

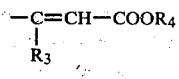

in which $R_3$ represents hydrogen atom, a lower alkyl group or phenyl group and $R_4$ represents an alkyl group;

when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when n is 3, $R_2$ represents an aromatic triacyl group or a trivalent group from an oxoacid; and when n is 4, $R_2$ represents an aromatic tetraacyl group, and A represents a group

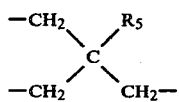

in which $R_5$ represents hydrogen atom or a lower alkyl group or, when n is 1, $R_5$ may represent together with $R_2$ a group

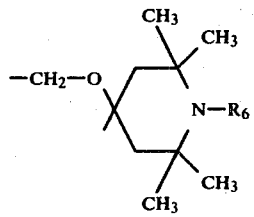

in which $R_6$ represents the same group as defined in $R_1$ and may be the same or different from $R_1$, or a group

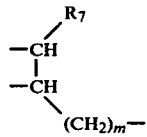

in which m is 1 or 2 and $R_7$ represents hydrogen atom or, when n and m are 1, $R_7$ represents methylene group together with $R_2$.

Murayama et al. U.S. Pat. No. 3,840,494, patented Oct. 8, 1974 provides acid esters of 4-piperidinol derivatives having the formula:

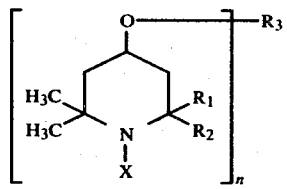

wherein:

$R_1$ and $R_2$ may be the same or different and represent an alkyl group of one to four carbon atoms or they may form, together with the carbon atom to which they are attached, a saturated alicyclic group or the group of the formula:

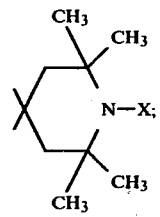

X is hydrogen atom, oxygen free radical (—O˙) or an alkyl group of one to four carbon atoms;

n is an integer of 1 through 4 inclusive; and $R_3$ represents, when n is 1, an acyl group derived from an aliphatic or aromatic monocarboxylic acid, when n is 2, a diacyl group derived from an aliphatic or aromatic dicarboxylic acid or carbonyl group, when n is 3, a triacyl group derived from an aliphatic or aromatic tricarboxylic acid or a trivalent group obtained by eliminating three hydroxyl groups from phosphoric acid, phosphorous acid or boric acid, and when n is 4 a tetraacyl group derived from an aromatic tetracarboxylic acid or a tetravalent group obtained by eliminating four hydroxyl groups from orthosilicic acid.

Murayama et al. U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al. U.S. Pat. No. 3,941,744 patented Mar. 2, 1976, disclose another variation of the piperidino spiro derivatives having the formula:

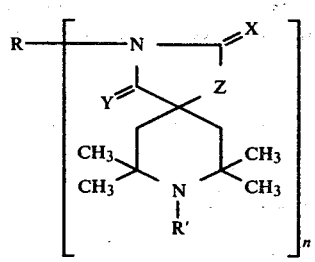

wherein

R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula=N—R" in which R" is hydrogen atom, an alkyl group or a substituted alkyl group;

Z represents oxygen atom or a group of the formula >N—R''' is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group, when n is 3, an alkanetriyl group, a tris-(acyloxyalkylene) group, an alkane-tris-(oxycarbonylalkyl) group or a group of the group

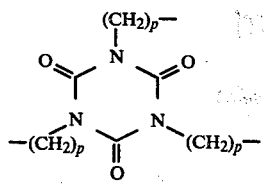

in which p is an integer of 1 through 8 inclusive, and when n is 4, an alkane tetrayl group, a tetrakis-(acyloxyalkylene) group or an alkanetetrakis-(oxycarbonylalkyl) group.

Murayama et al. U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

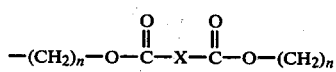

in which n is an integer of 1 or 2 and X is an alkylene group, or o-, m- or p-phenylene group or the carbon atoms of CO groups may be directly joined in the absence of X or a group of the formula:

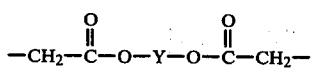

in which Y is an alkylene group or o-, m- or p-phenylene group.

Ramey et al. U.S. Pat. No. 3,875,169 patented Apr. 1, 1975 and U.S. Pat. No. 3,991,012 patented Nov. 9, 1976 provide bicyclic hindered amines of the formula:

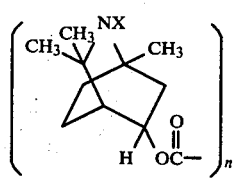

wherein
X is H, O, or OH,
n is 1 or 2, and (a) when n is 1, R is straight- or branched-chain alkyl having one to twenty carbon atoms, phenyl or phenyl substituted by one or more lower alkyl groups, and (b) when n is 2, R is straight- or branched-chain alkylene having one to twenty carbon atoms, phenylene or phenylene substituted by one or more lower alkyl groups.

Preferred compounds of formula I are those wherein X is H or O; and n is 1 or 2; and (a) when n is 1, R is n-alkyl having one to twenty atoms, and (b) when n is 2, R is n-alkylene having one to twelve carbon atoms.

Ramey et al. U.S. Pat. No. 3,907,803 patented Sept. 23, 1975 and U.S. Pat. No. 4,001,181 patented Jan. 4, 1977 provide hindered piperidine carboxamide acids and metal salts thereof of the formula:

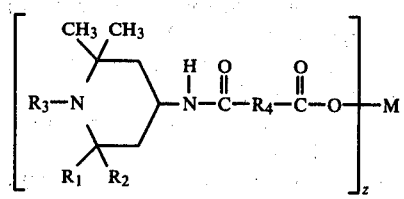

wherein
$R_1$ and $R_2$ independently of each other are straight- or branched-chain lower alkyl having one to six carbon atoms, or together with the carbon to which they are bound form a cyclopentyl or cyclohexyl ring, which is unsubstituted or substituted with a methyl group, $R_3$ is hydrogen, alkyl having one to twelve carbon atoms, β-methoxyethyl alkenyl having three or four carbon atoms, propargyl, benzyl, or alkyl-substituted benzyl, $R_4$ is straight- or branched-chain alkylene having one to eight carbon atoms, phenylene, phenylene substituted with one or more alkyl groups, or the group $-(CH_2)_mY(CH_2)_n-$, wherein Y is oxygen or sulfur and m and n independently of each other are an integer of from 1 to 3, M is hydrogen or a metal selected from the group consisting of barium, nickel, manganese, calcium, zinc, iron, sodium, cobalt, tin, dialkyltin, and z has a value of from 1 to 4, the value of z being the same as the available valence of M.

Ramey et al U.S. Pat. Nos. 3,899,491, patented Aug. 12, 1975 and U.S. Pat. No. 3,920,659, patented Nov. 18, 1975, disclose alkyl alkanoate derivatives of substituted piperazines and substituted piperazinodiones. The substituted piperazines of U.S. Pat. No. 3,899,491 have the formula:

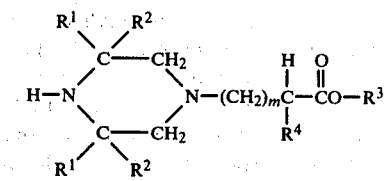

wherein
$R^1$ and $R^2$ are methyl or together with the carbon to which they are bound form a mono-cyclic ring system having five or six carbon atoms;
$R^3$ is an alkyl group of from one to twenty atoms;
$R^4$ is hydrogen or methyl, and
m is 0 or 1.

The substituted piperazinodiones of No. 3,920,659 have the formula:

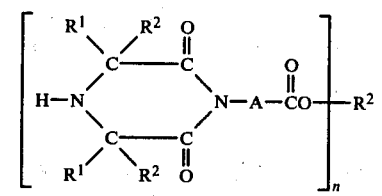

wherein $R^1$ and $R^2$ are independently of each other methyl or ethyl or together with the carbon to which they are bound form a cyclopentyl or cyclohexyl ring, which is unsubstituted or substituted with a methyl group;

n is an integer of from 1 to 2;

when n is 1, $R^3$ is an alkyl group of from one to twenty carbon atoms;

when n is 2, $R^3$ is an alkylene group of from two to eight carbon atoms; and

A is a straight or branched chain (lower) alkylene group containing from one to six carbon atoms with the limitation that the terminals of said alkylene group bear only hydrogen or one (lower) alkyl group.

Ramey et al. U.S. Pat. No. 3,920,661, patented Nov. 18, 1975 disclose dicarboxylic acids and salts in which one carboxylic acid group is esterified with a 2,2,6,6-tetrasubstituted-4-hydroxy piperidine and having the formula:

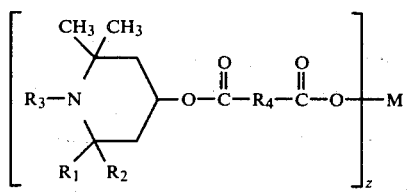

wherein $R_1$ and $R_2$ independently of each other are straight-or branched-chain alkyl having from one to six carbon atoms, or together with the carbon to which they are bound form a cyclopentyl or cyclohexyl ring, which is unsubstituted or substituted with a methyl group;

$R_3$ is hydrogen, alkyl having from one to twelve carbon atoms, β-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_mY(CH_2)_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Minagawa et al., U.S. Pat. No. 4,128,608, patented Dec. 5, 1978, provides 2,2,6,6-tetramethyl-4-piperidyl spiro aliphatic ethers useful as stabilizers for organic polymeric materials, and having the general formula:

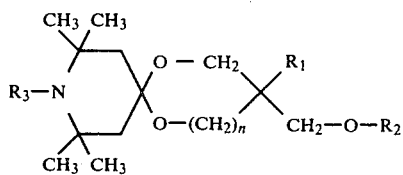

wherein:

$R_1$ is selected from the group consisting of hydrogen, lower alkyl and lower hydroxyalkyl having one or two carbon atoms; $R_2$ is

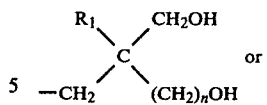

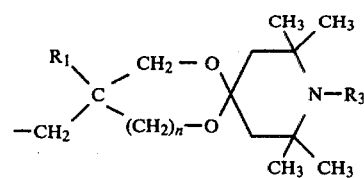

$R_3$ is selected from the group consisting of hydrogen and O; and n is 0 to 1.

In accordance with the instant invention, 2,2,6,6-tetramethyl-4-piperidyl-bis-spiro aliphatic ethers are provided, useful as stabilizers for organic polymeric materials, having the general formula:

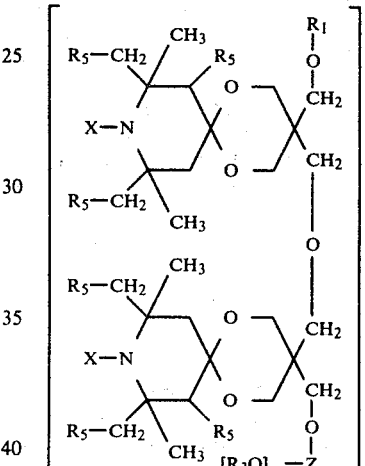

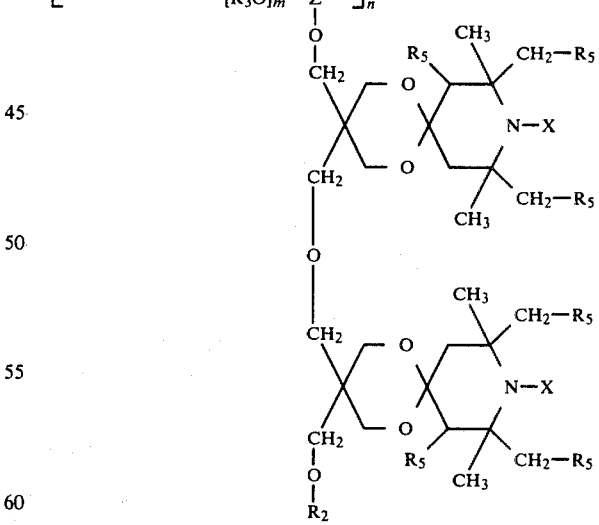

$R_1$ and $R_2$ each are selected from the group consisting of hydrogen, alkyl, hydroxyalkyl, acyl, aryl, alkaryl, carbamoyl having one to about twenty carbon atoms;

Z is selected from the group consisting of alkylene; arylene; alkylene-arylene;

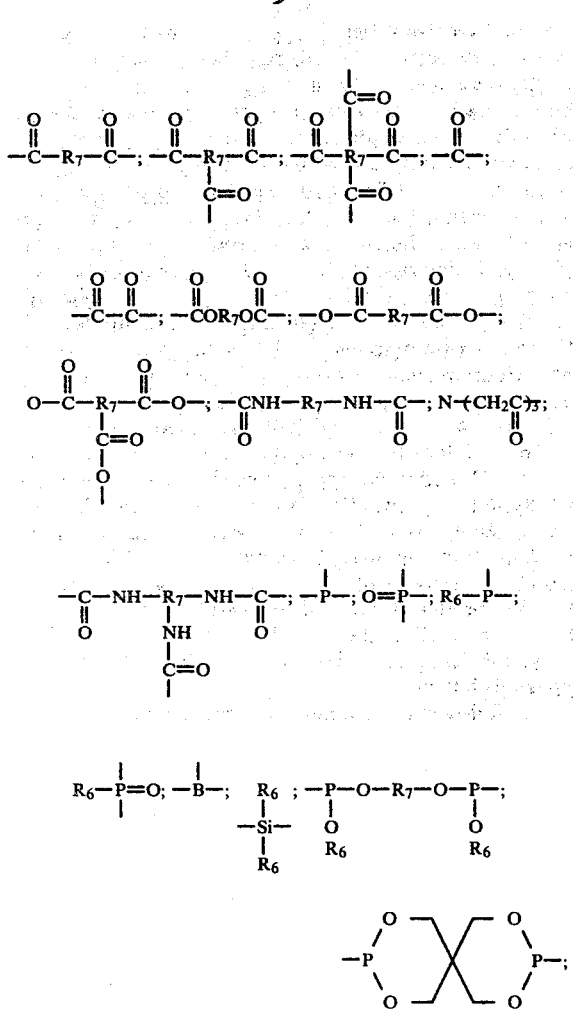

$R_6$ being alkyl or aryl and $R_7$ being alkylene, cycloalkylene or arylene, each having from one to about twenty carbon atoms;

$R_3$ is selected from the group consisting of alkyl and aryl having from one to about eighteen carbon atoms; and

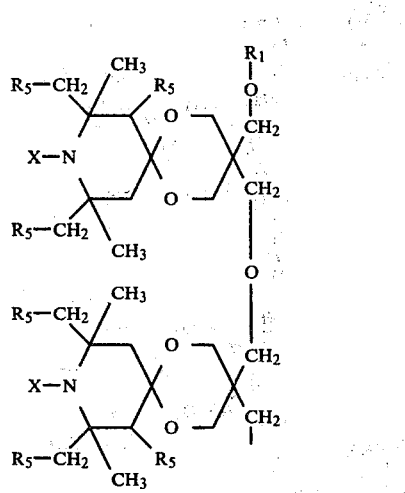

$R_5$ is selected from the group consisting of hydrogen and lower alkyl;

X is selected from the group consisting of hydrogen, oxyl (O·) and lower alkyl having from one to about five carbon atoms;

m is zero, one or two; and n is a number from zero to ten.

Exemplary $R_1$, $R_2$ and $R_3$ alkyl include methyl, ethyl, propyl, butyl, amyl, hexyl, octyl, 2-ethylhexyl, isooctyl, decyl, dodecyl, tetradecyl, and octadecyl, and hydroxyethyl.

Exemplary $R_1$, $R_2$ and $R_3$ aryl include phenyl, benzyl, phenethyl and naphthyl.

Exemplary $R_1$ and $R_2$ alkaryl include tolyl, xylyl, butylphenyl and nonylphenyl.

Exemplary $R_1$ and $R_2$ acyl include formyl, acetyl, propionyl, butyryl, pivalyl, 2-ethylhexanoyl, octanoyl, lauroyl, palmitoyl, stearoyl, acryloyl, crotonoyl, oleoyl, acetoacetyl, levulinyl, pyruvyl, ketostearoyl, aminoacetyl, dodecylmercaptopropionyl, 3,5-di-t-butyl-4-hydroxyphenylpropionyl, benzoyl, toluyl, 4-t-butylbenzoyl, 3,5-di-t-butyl-4-hydroxybenzoyl, nicotinoyl, isonicotinoyl, 2,2,6,6-tetramethylpiperidine-4-carboxyl,3,8,8,10,10-pentamethyl-9-aza-1,5-dioxa-spiro (5,5)-undecane-3-carboxyl, oxaloyl, malonoyl, succinoyl, glutaroyl, adipoyl, sebacoyl, dodecanedicarboxyl, maleoyl, phthaloyl, isophthaloyl, terephthaloyl, tricarballoyl, butanetricarboxyl, butenetricarboxyl, trimellitoyl, butanetetracarboxyl, pyromellitoyl, thiophenedicarboxyl, furanedicarboxyl and partial esters thereof.

Exemplary $R_1$ and $R_2$ carbamoyl include carbamoyl groups derived from propylisocyanate, butylisocyanate, hexadecylisocyanate, octadecylisocyanate, phenylisocyanate, tolylisocyanate, 3,4-dichlorophenylisocyanate, nitrophenylisocyanate, tosylisocyanate, cyclohexylisocyanate, hexamethylenediisocyanate, lysinediisocyanate, phenyldiisocyanate, tolylenediisocyanate, diphenyletherdiisocyanate, xylylenediisocyanate, 3-isocyanatemethyl-3,5,6-trimethylcyclohexylisocyanate, bis(isocyanatemethyl) cyclohexane and 3-(2'-isocyanatecyclohexyl) propylisocyanate. When diisocyanate is used, one of the isocyanate groups may remain, or be reacted with compounds having active hydrogens, such as alcohols, phenols or amines.

Exemplary $R_1$ and $R_2$ oxy acid groups include those derived from phosphorous acid, phosphoric acid, (mono-organo) phosphonous acid, (mono-organo) phosphonic acid, (diorgano) phosphinous acid, (diorgano) phosphinic acid, (mono-organo) silicic acid, boric acid and esters thereof.

Exemplary Z alkylene include methylene, ethylene, propylene, butylene, hexamethylene and octamethylene.

Exemplary Z arylene include phenylene and biphenylene.

Exemplary Z polyacyl include diacyl groups derived from oxalic acid, malonic acid, succinic acid, glutaric acid, adipic acid, sebacic acid, dodecanedicarboxylic acid, eicosane dicarboxylic acid, tartaric acid, maleic acid, phthalic acid, isophthalic acid, terephthalic acid, iminodiacetic acid, thiodipropionic acid, diglycolic acid, tetrahydrophthalic acid, endomethylenetetrahydrophthalic acid, thiophenedicarboxylic acid, furandicarboxylic acid, dicarboxyethylpiperidine, tricarballic acid, butanetricarboxylic acid, butenetricarboxylic acid, citric acid, trimellitic acid, butanetetracarboxylic acid and pyromellitic acid.

Exemplary Z polycarbamoyl include polycarbamoyl groups derived from hexamethylenediisocyanate, lysinediisocyanate, phenyldiisocyanate, tolylenediisocyanate, diphenyletherdiisocyanate, xylylenediisocyanate, 3-isocyanatemethyl-3,5,5-trimethylcyclohexylisocyanate, bis(isocyanatemethyl) cyclohexane, and 3-(2'-isocyanatecyclohexyl) propylisocyanate.

Exemplary Z oxyacid groups include groups derived from phosphorous acid, phosphoric acid, (mono-organo) phosphonous acid, (mono-organo) phosphonic acid, boric acid, (mono-organo) silicic acid and oxyacid groups linked together by polyol or polyphenol groups, in a linear or spiro structure (as in dipentaerythritol).

$R_5$ alkyl include methyl, ethyl, propyl, isopropyl and butyl.

$R_6$ alkyl and aryl are as exemplified in $R_1$, $R_2$ and $R_3$ above.

Exemplary $R_7$ alkylene include residues of polyols such as ethylene glycol, diethylene glycol, triethylene glycol, 1,2-propanediol, 1,3-propanediol, 1,2-butanediol, 1,3-butanediol, 1,4-butanediol, neopentyl glycol, thiodiethylene glycol, 1,6-hexanediol, 1,10-decanediol, 1,4-cyclohexanediol, 1,4-cyclohexanedimethanol, 1,4-phenyl-dimethanol, hydrogenated Bisphenol-A, glycerol, trimethylol methane, trimethylol ethane and tris (2-hydroxyethyl)-isocyanurate.

Exemplary $R_7$ arylene include residues of polyphenols such as hydroquinone, 4,4'-isopropylidenediphenol (Bisphenol A), 4,4'-cyclohexylidene-diphenol, 4,4'-methylene-bisphenol, 4,4'-sulfo-bisphenol, 2,5-di-t-butyl-hydroquinone, 2,3,6-trimethylhydroquinone, 2-methylresorcinol, 2,2'-methylene-bis (4-methyl-6-t-butylphenol), 2,2'-methylene-bis (4-ethyl-6-t-butylphenol), 2,2'-methylene-bis [4-methyl-6-(α-methylcyclohexyl)phenyl], 2,2'-n-butylidene-bis (4,6-di-methylphenol), bis-1,1-(2'-hydroxy-3',5'-di-methylphenyl)-3,5,5-trimethylhexane, 2,2'-cyclohexylidene-bis (4-ethyl-6-t-butylphenol) 2,2'-isopropyl benzylidene-bis (4-ethyl-6-t-butylphenol), 2,2'-thio-bis(4-t-butyl-6-methylphenol), 2,2'-thio-bis (4-methyl-6-t-butylphenol), 2,2'-thio-bis (4,6-di-t-butylphenol), 4,4'-methylene-bis (2-methyl-6-t-butylphenol), 4,4'-isopropylidene-bis (2-phenylethylphenol), 4,4'-n-butylidene-bis (3-methyl-6-t-butylphenol), 4,4'-cyclohexylidene-bis (2-t-butylphenol), 4,4'-cyclohexylidene-bis (2-cyclohexylphenol), 4,4'-benzylidene-bis (2-t-butyl-5-methylphenol), 4,4'-oxa-bis (3-methyl-6-isopropylphenol), 4,4'-thio-bis (2-methyl-6-t-butylphenol), 4,4'-thio-bis (3-methyl-6-t-butylphenol), 4,4'-sulfo-bis (3-methyl-6-butylphenol), bis (2-methyl-4-hydroxy-5-t-butylbenzyl) sulfide, 1,1,3-tris (2'-methyl-4'-hydroxy-5'-t-butylphenyl) butane, 2,2-bis (3'-t-butyl-4'-hydroxyphenyl)-4-(3'',5''-di-t-butyl-4''-hydroxyphenyl) butane and 2,2-bis (2'-methyl-5'-t-butyl-4'-hydroxyphenyl)-4-(3'',5''-di-t-butyl-4'-hydroxyphenyl) butane.

The following compounds are exemplary:

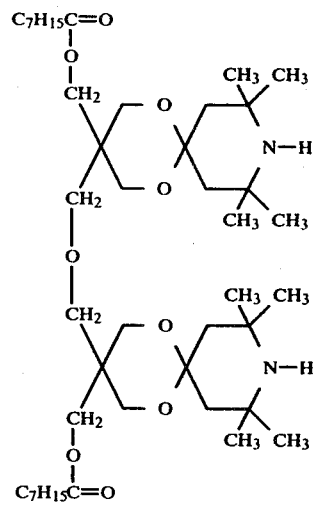

No. 1

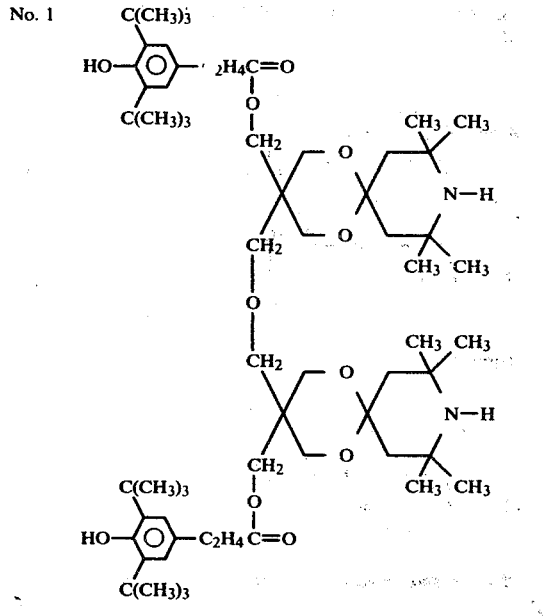

No. 2

-continued
No. 3
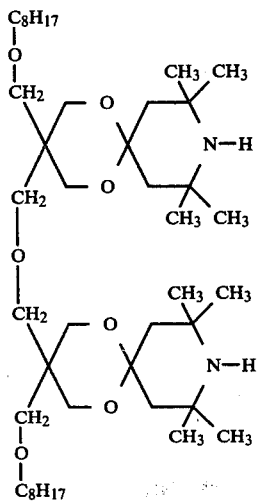
No. 4
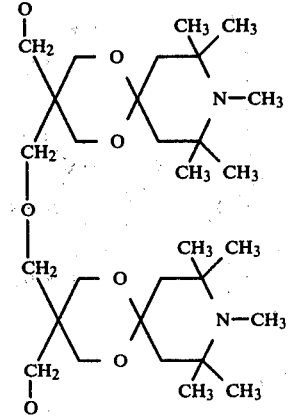
No. 5
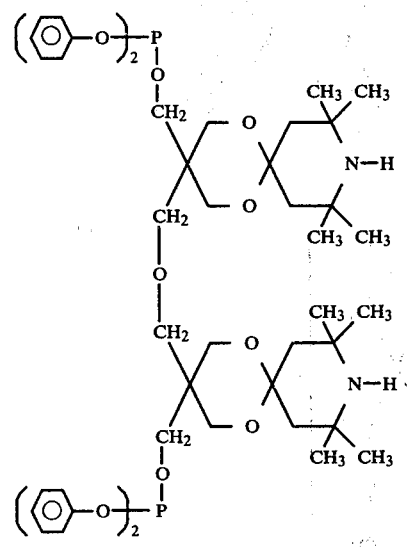
No. 6
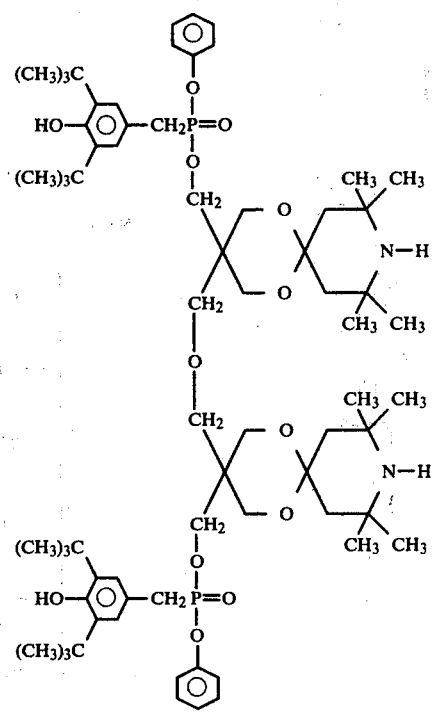

-continued
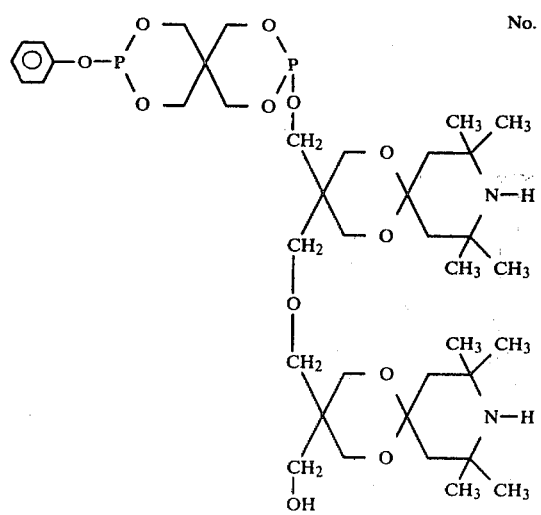
No. 7
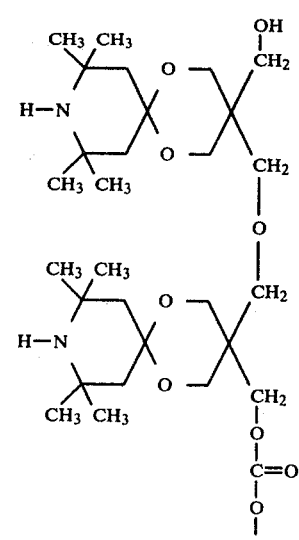
No. 8
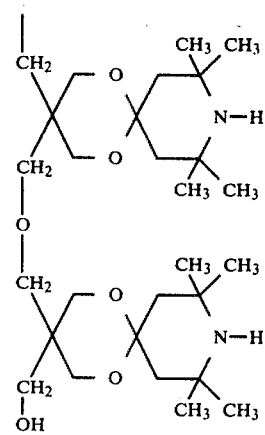
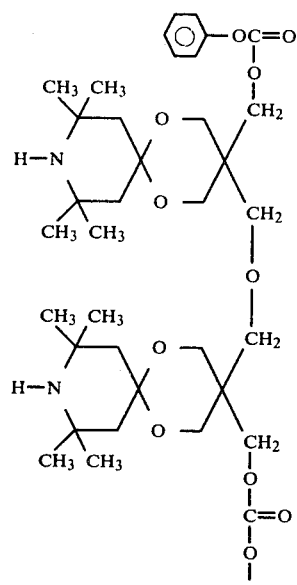
No. 9
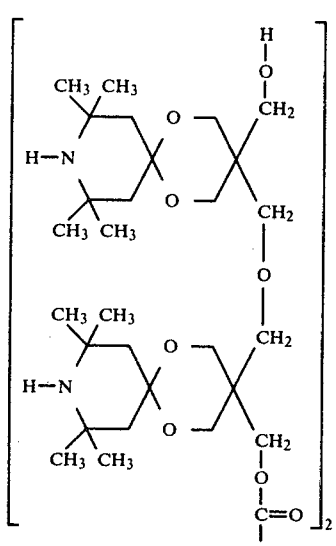
No. 10

-continued
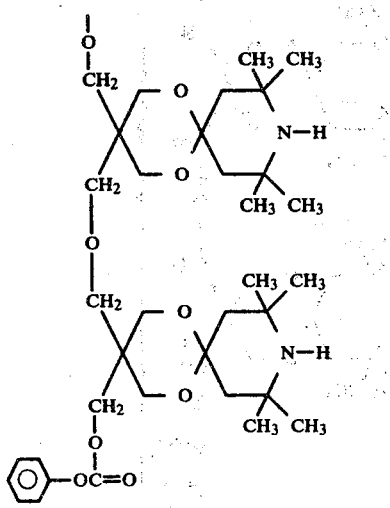 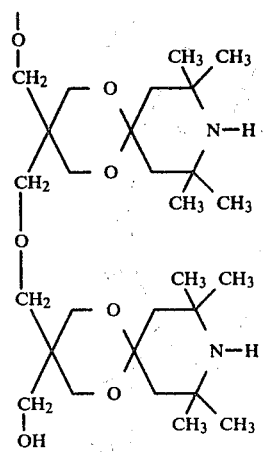
No. 11 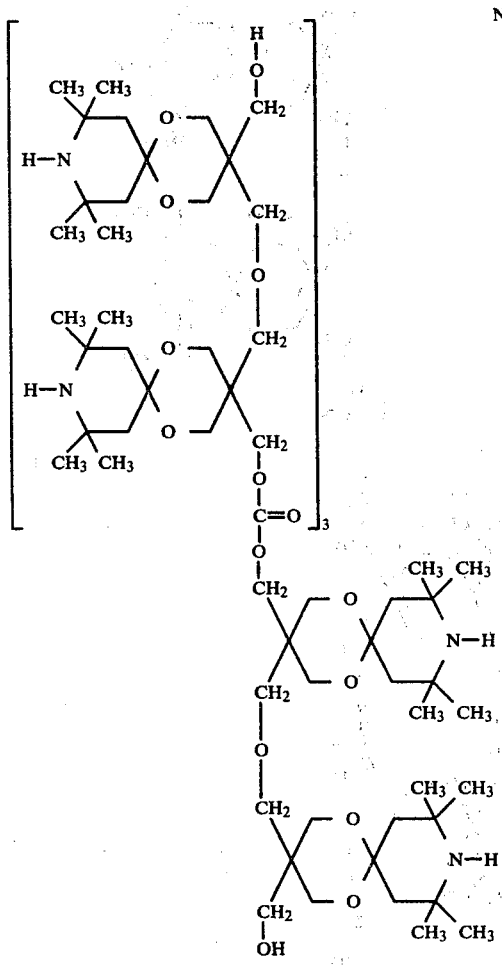 No. 12 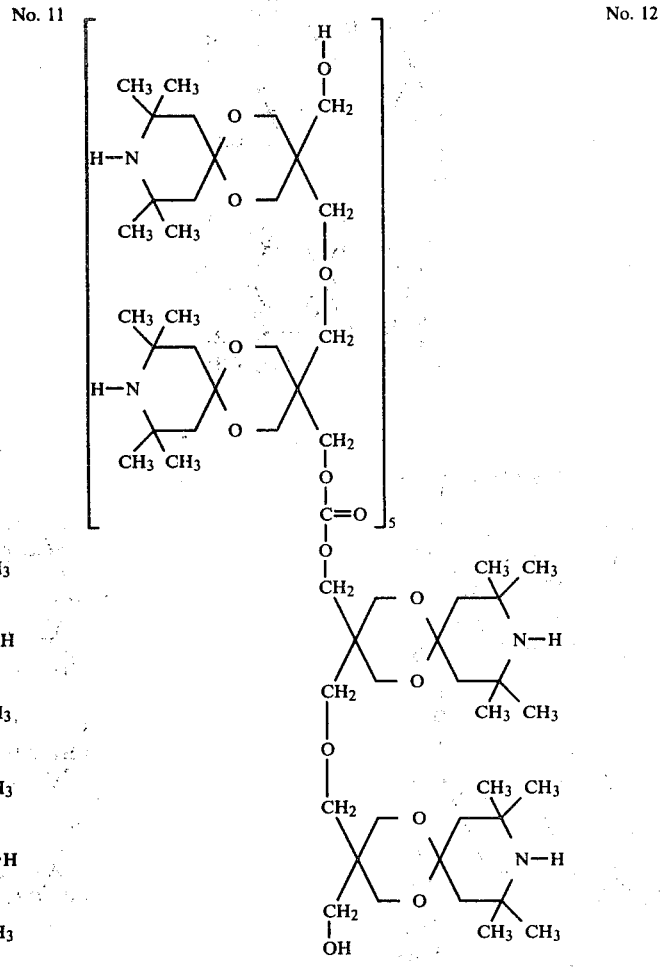

-continued
No. 13
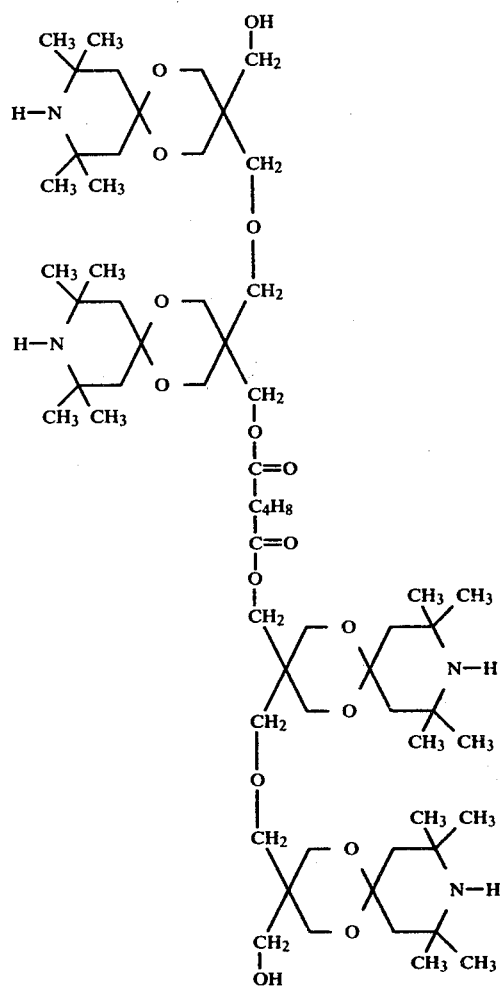
No. 14
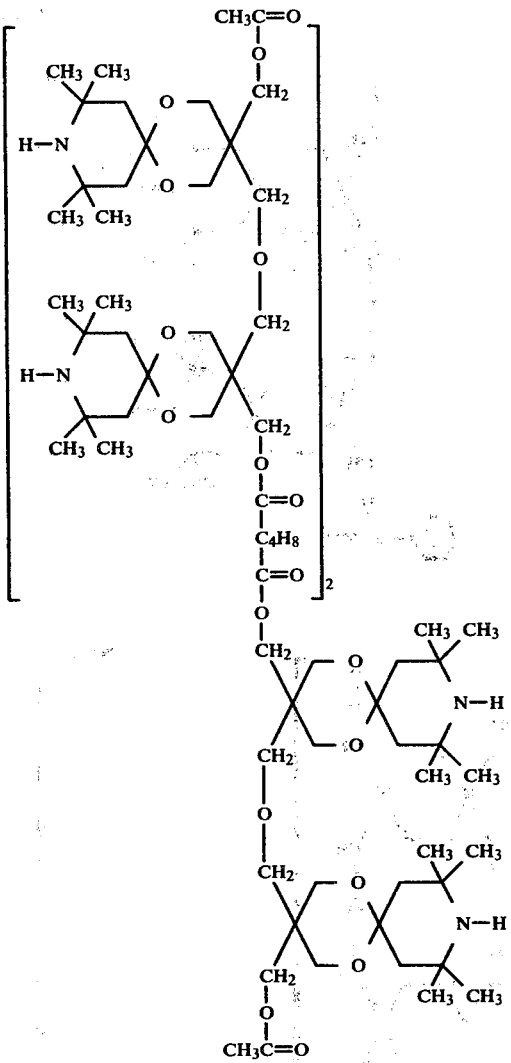
No. 15
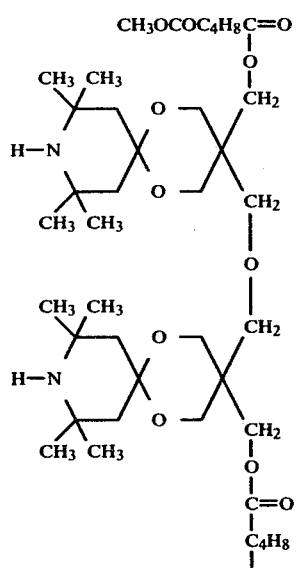
No. 16
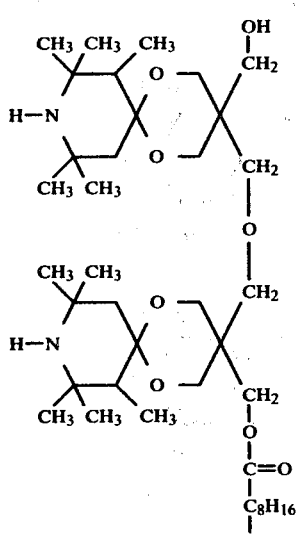

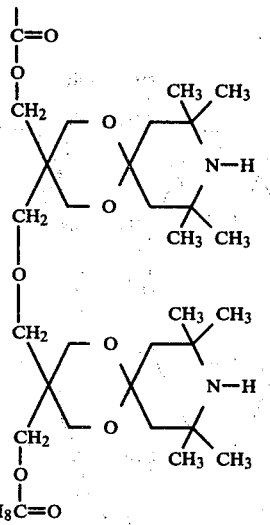
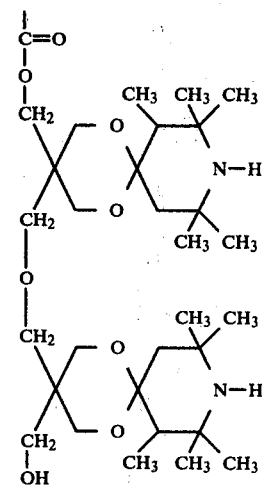
No. 17
No. 18
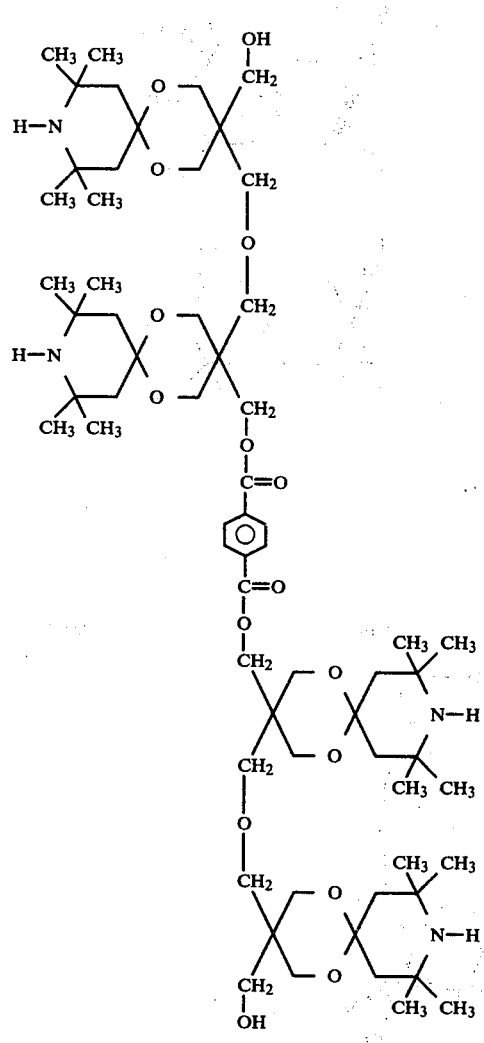
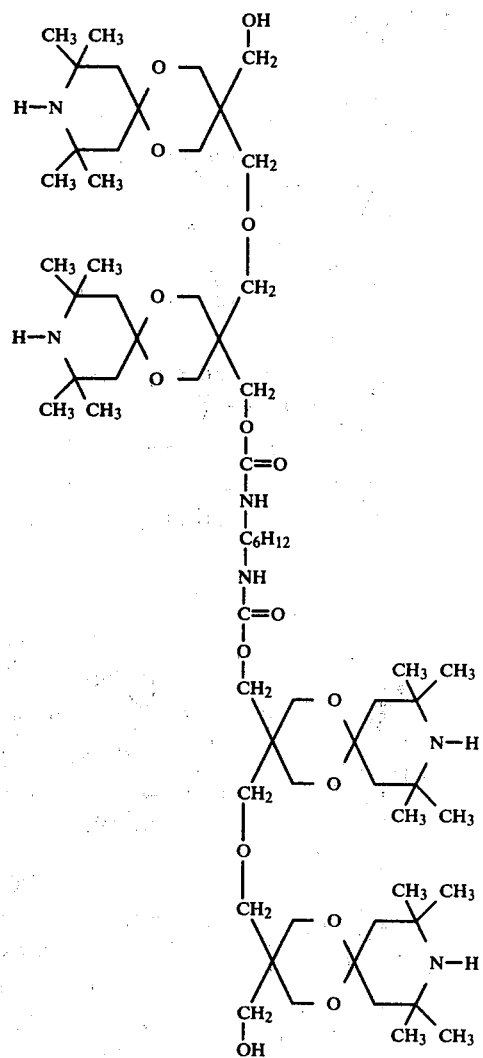

No. 19
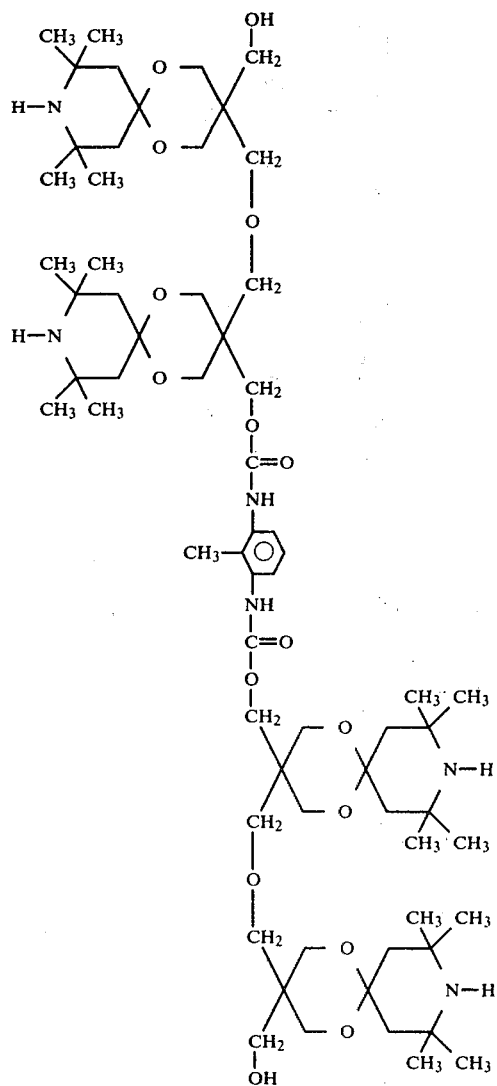
No. 20
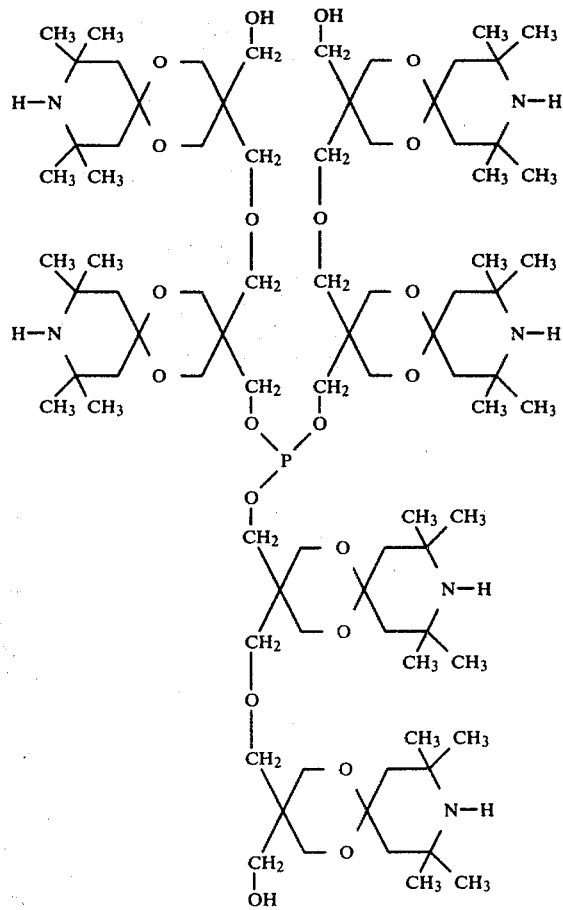
No. 21
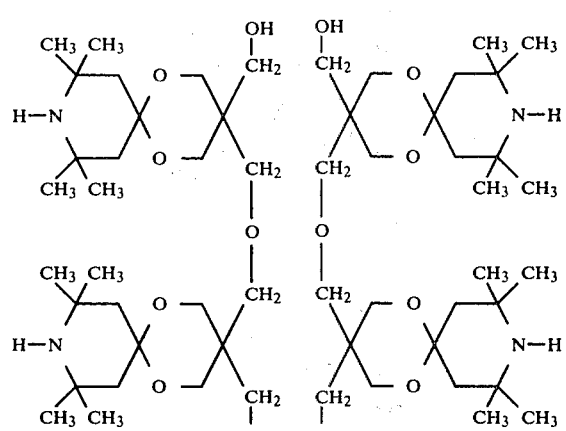
No. 22
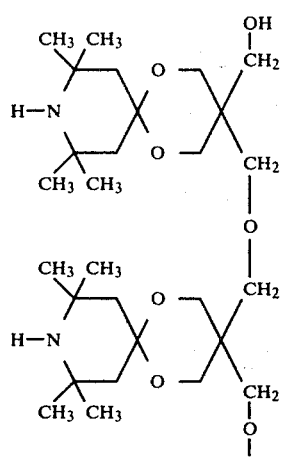

-continued
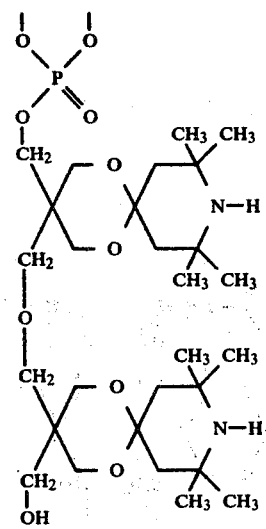
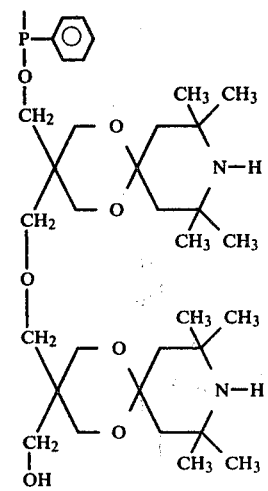
No. 23
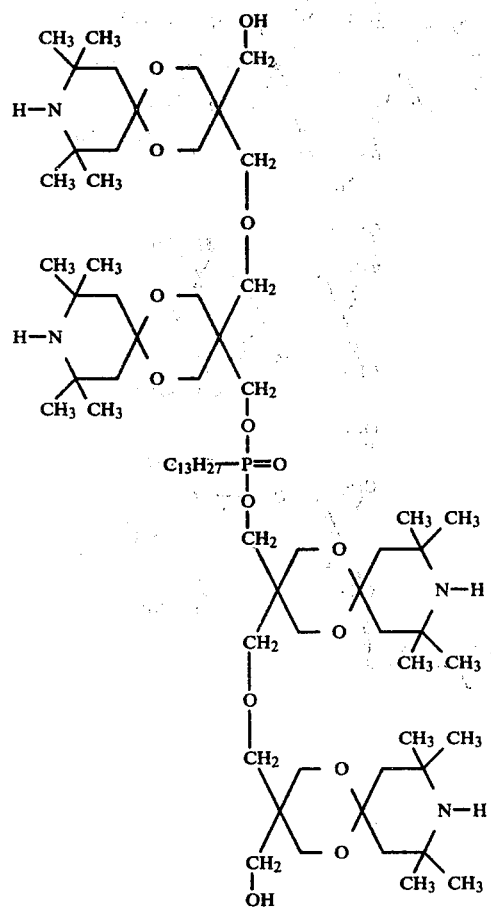
No. 24
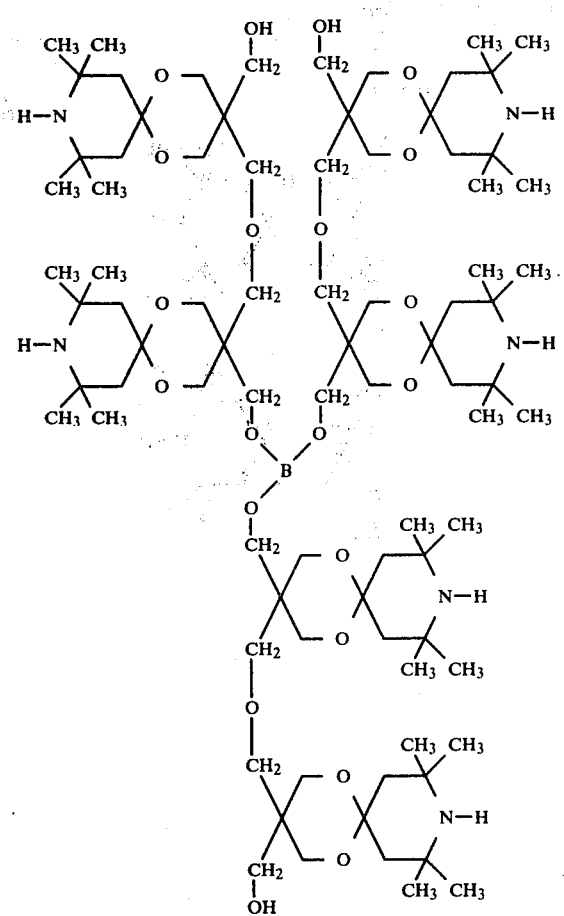

-continued
No. 25
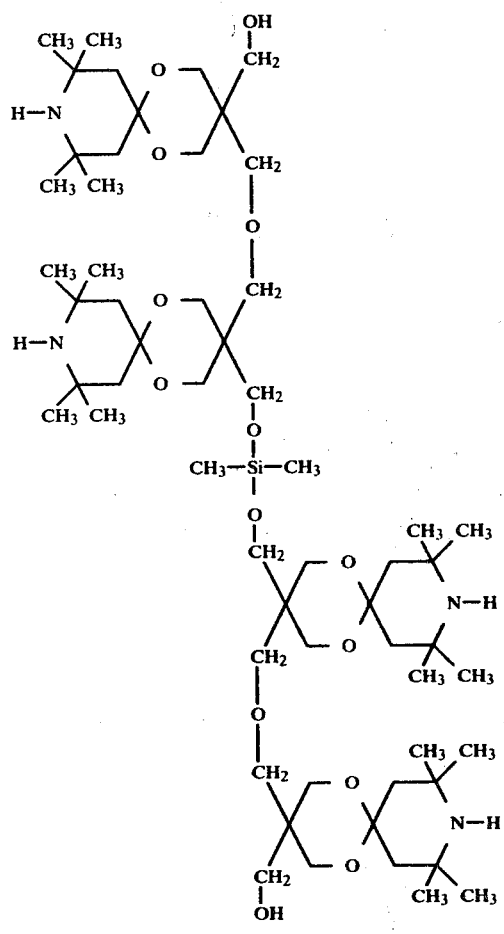
No. 26
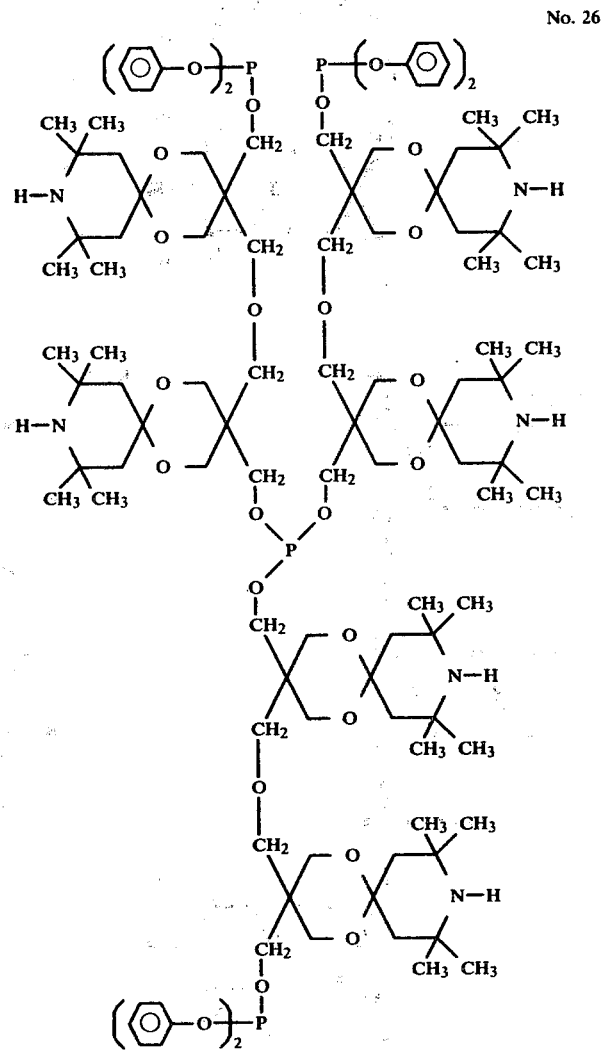

-continued
No. 27
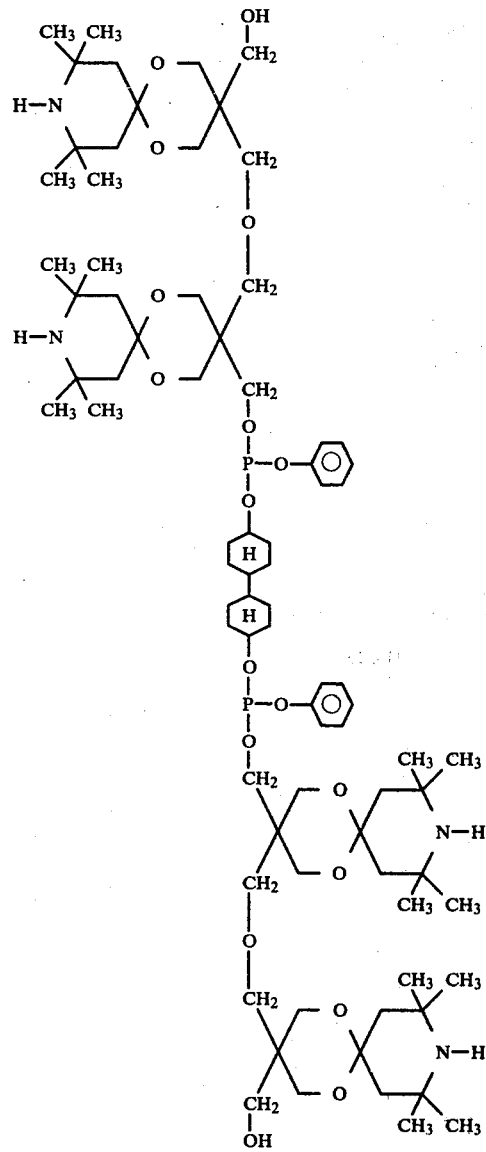
No. 28
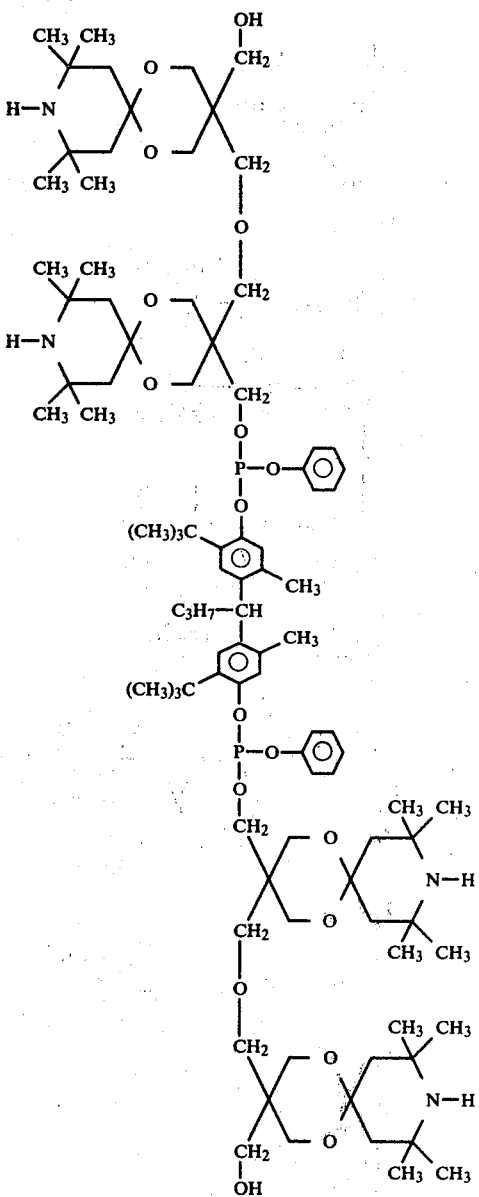
No. 29
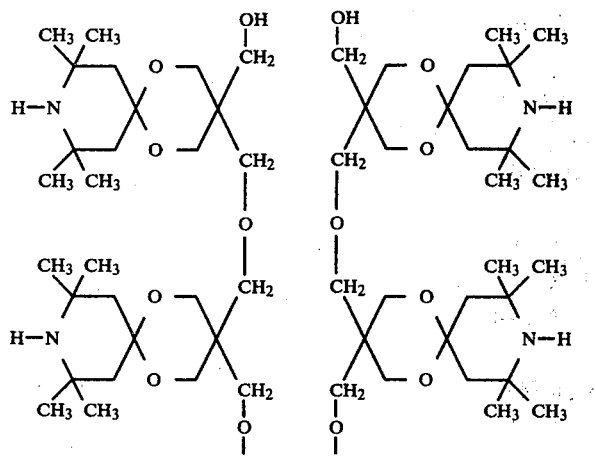

-continued
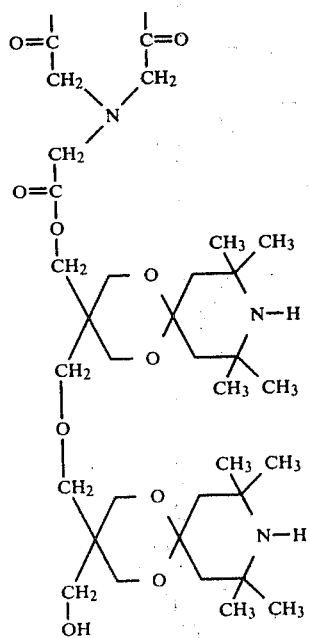
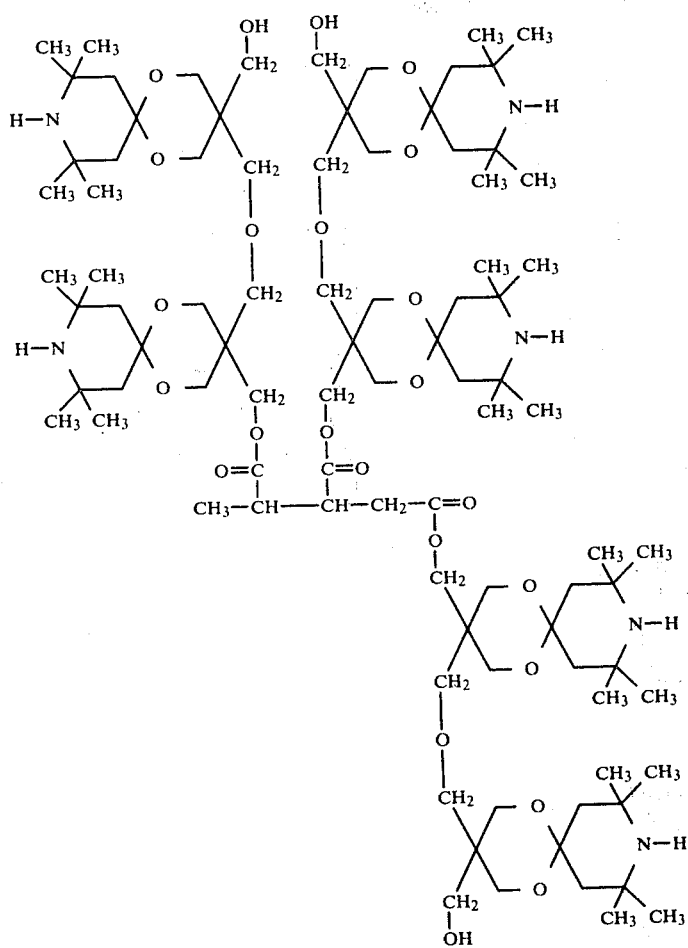
No. 30

-continued
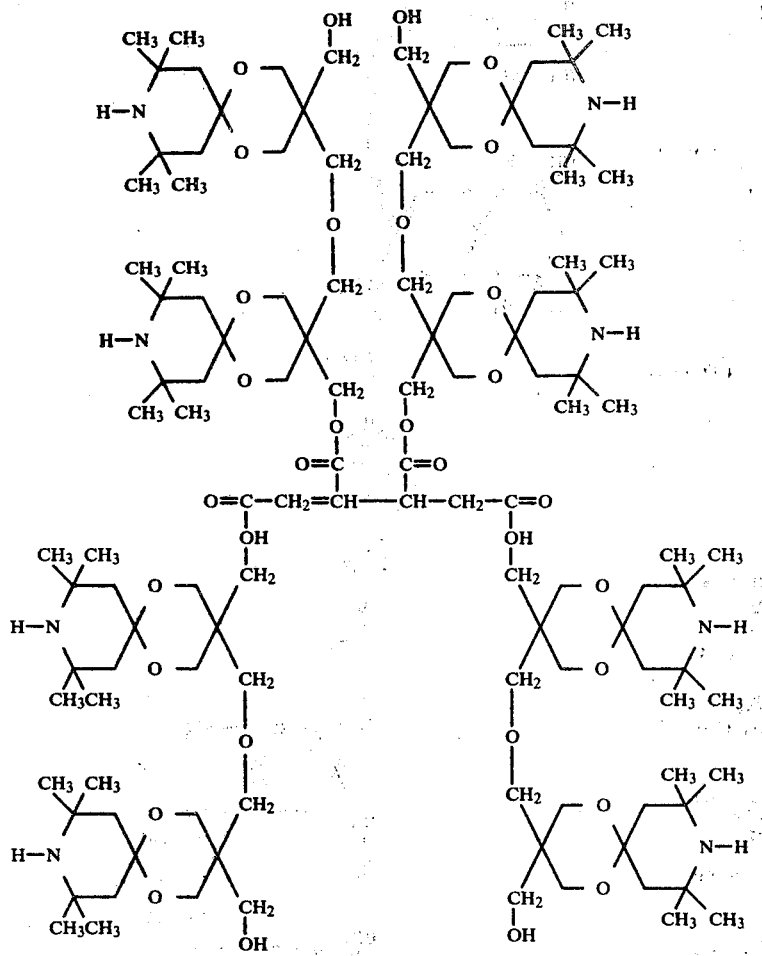
No. 31

-continued
No. 32
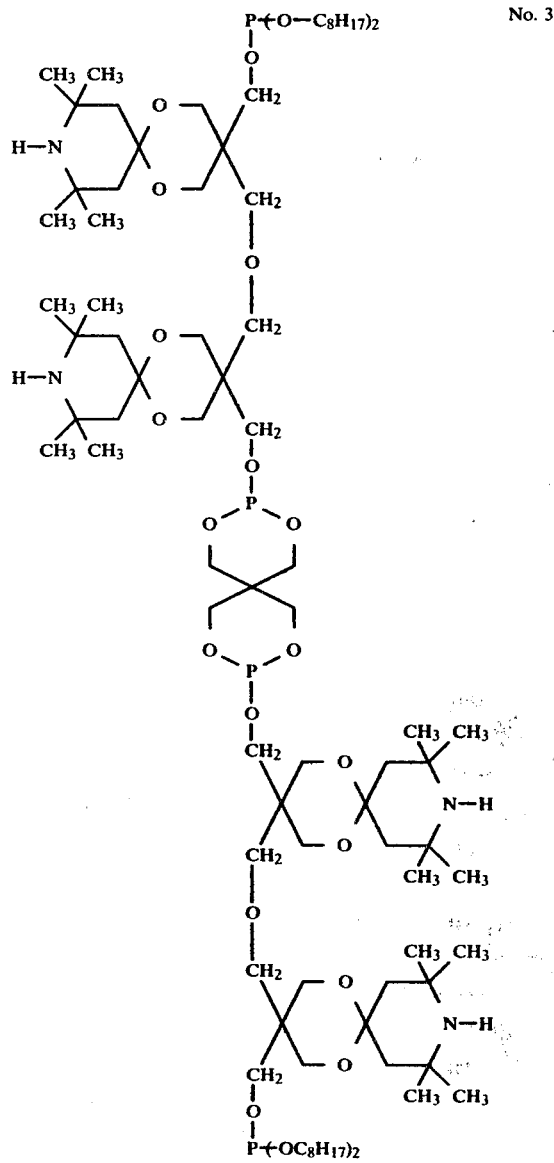
No. 33
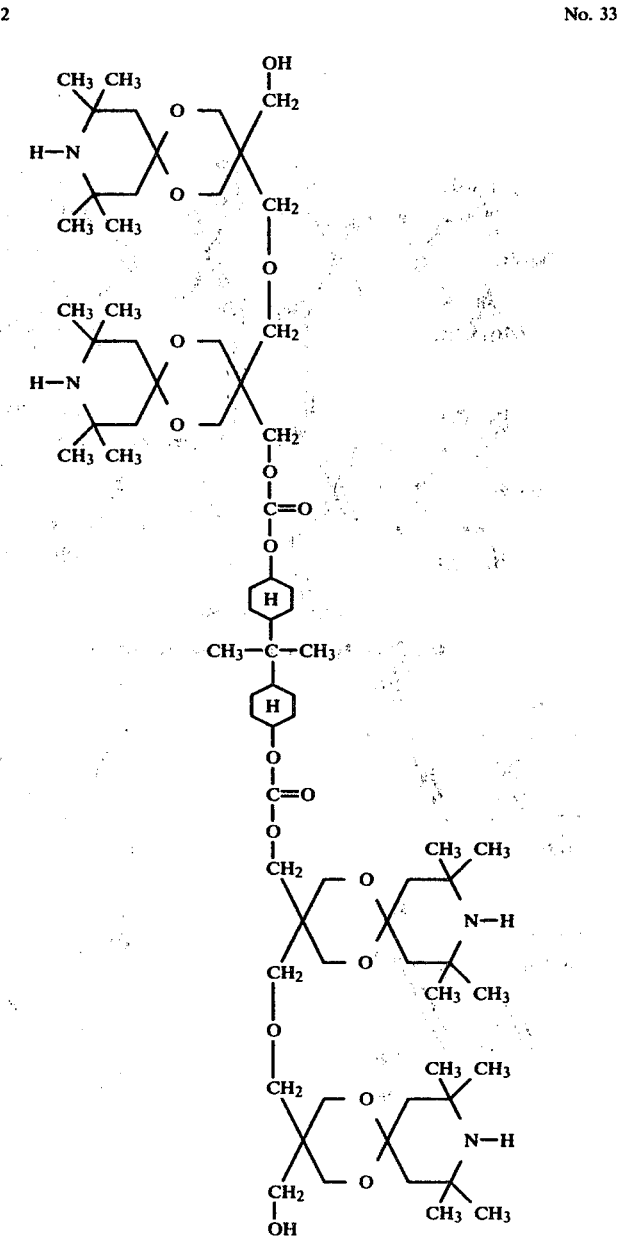

-continued
No. 34
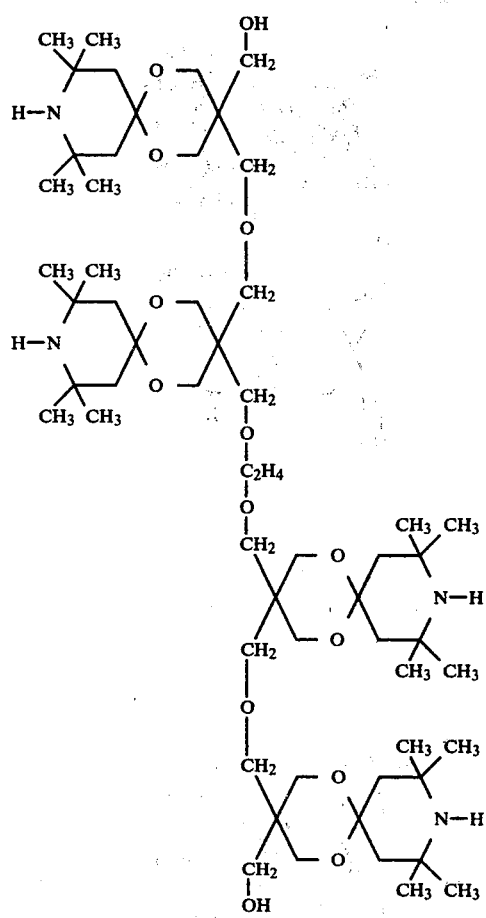
No. 35
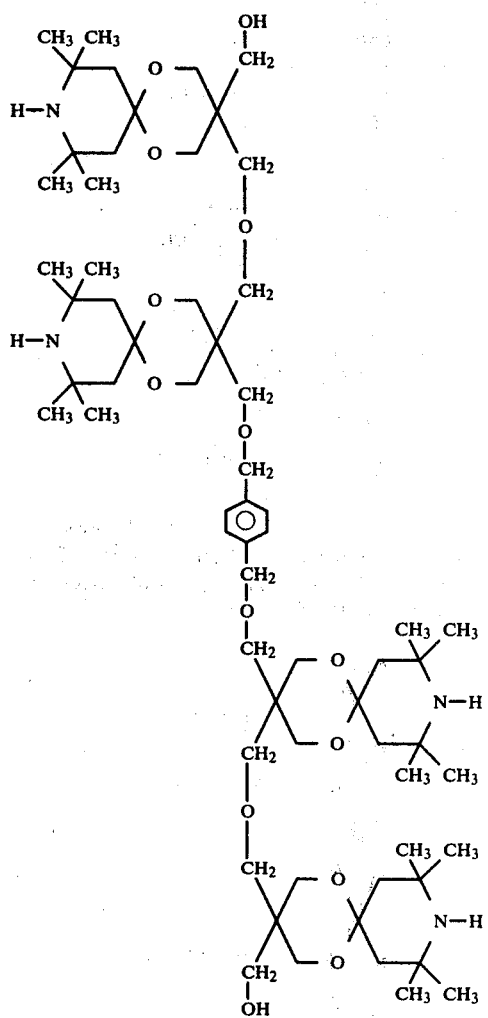
No. 36
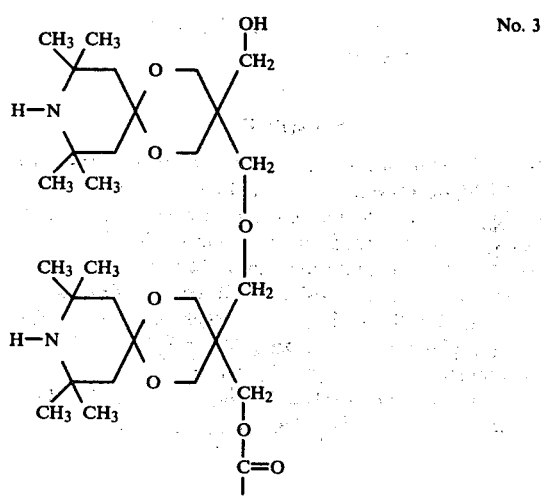
No. 37
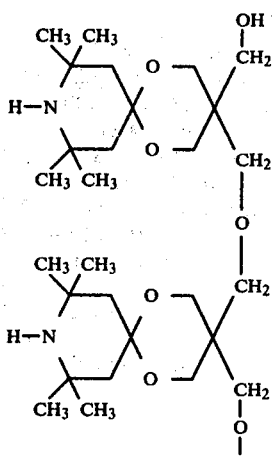

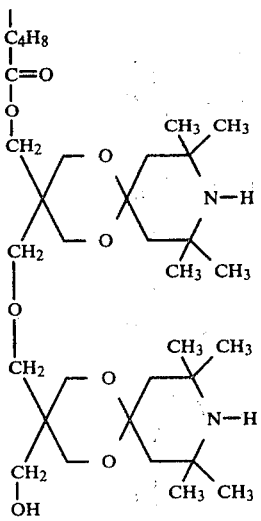

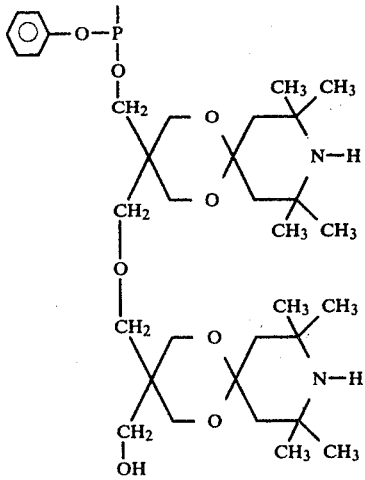

The compounds of the invention can easily be prepared by conventional esterification or etherification of the corresponding bis-(2,2,6,6-tetraalkyl piperidyl alcohol) ether, represented by the formula:

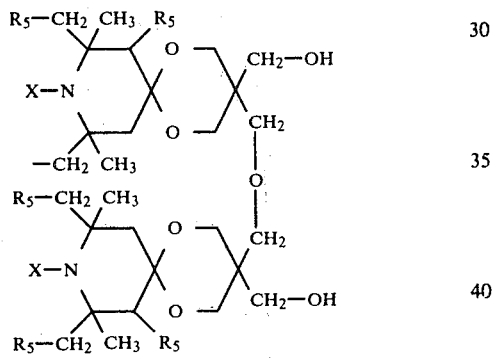

The following Examples illustrate the preparation of the exemplary compounds of the invention noted above:

EXAMPLE A 5.3 g of the bis-ketal 2,2,6,6-tetramethyl-4-piperidone with dipentaerythritol, 4.7 g (1.5 eq) of methyl caprylate, 10 ml of xylene and 0.2 ml of a 28% methanol solution of sodium methoxide were heated and stirred for five hours at 150° C. under a stream of nitrogen. After cooling, the solution was extracted with ether, washed with water, dried and stripped. 6.2 g (82%) of yellow viscous liquid was obtained. High speed liquid chromatographic analysis showed that it consisted of only one component.

IR Analysis: $\nu_{NH}$: 3325 cm$^{-1}$ $\nu_{C=O}$ 1740 cm$^{-1}$ $\nu_{C-O}$ (ketal) 1100 cm$^{-1}$ The results demonstrated that the compound had the structure:

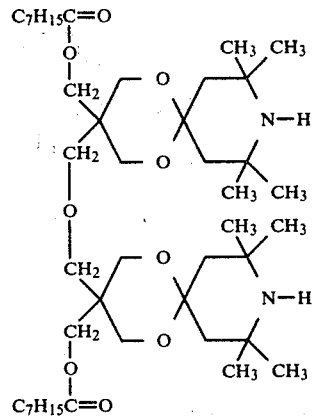

EXAMPLE B 10.6 g (0.02 mole) of the bis-ketal of dipentaerythritol with 2,2,6,6-tetramethyl-4-piperidone, 2.1 g (0.01 mole) of diphenylcarbonate and 0.03 g of potassium carbonate were heated and stirred for one hour at 120° C. under a stream of nitrogen, and the phenol liberated as a by-product was removed by distillation for one hour at 140° C. 2 mm Hg. 100% of the phenol was removed. After cooling, a glassy solid, softening point 74° C. to 87° C., was obtained.

The results demonstrated that this compound had the formula:

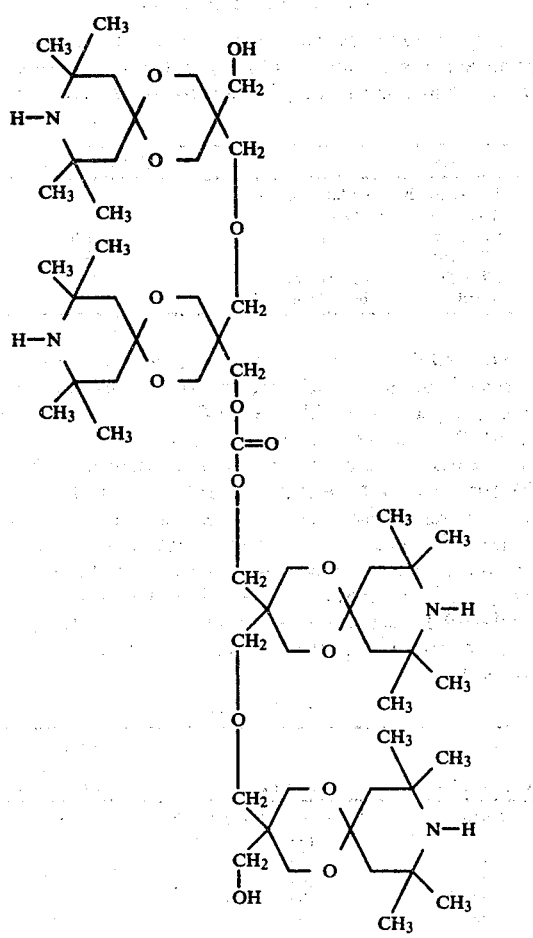

The 2,2,6,6-tetraalkyl-4-piperidyl-bis-spiro ethers of the invention are effective stabilizers to enhance the resistance to deterioration due to light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer, polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycolterephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The piperidyl-bis-spiro ethers of the invention can be used as a stabilizer in an amount within the range from about 0.001 to about 10 parts by weight, preferably from 0.01 to 5 parts by weight, per 100 parts by weight of polymer.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadiene-styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flame-proofing agents, pigments and fillers, can be employed.

The following Examples in the opinion of the inventors represent preferred embodiments of synthetic resin compositions in accordance with the invention:

EXAMPLES 1 to 5

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris (nonyl phenyl) phosphite | 0.2 |
| Ca stearate | 1.0 |
| Zn stearate | 0.1 |
| Stabilizer as shown in Table I | 0.2 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for a total of ten stabilizers in accordance with the invention, having the formulae indicated in Table I, in comparison with two controls, oxabis (9-aza-3-hydroxymethyl-8,8,10,10-tetramethyl-1,5-dioxaspiro[5,5]-3-undecylmethane), and bis(9-aza-3-ethyl-8,8,10,10-tetramethyl-1,5-dioxaspiro[5,5]-3-undecylmethyl)carbonate.

The following results were obtained:

TABLE I

| Example No. | Stabilizer | Hours to failure |
|---|---|---|
| Control 1 | None | 180 |
| Control 2 | Bis (9-aza-3-ethyl-8,8,10,10-tetramethyl-1,5-dioxaspiro [5,5]-3-undecylmethyl) carbonate | 260 |
| 1 | No. 1 | 770 |
| 2 | No. 5 | 810 |
| 3 | No. 7 | 820 |
| 4 | No. 10 | 880 |
| 5 | No. 14 | 850 |
| 6 | No. 20 | 820 |
| 7 | No. 27 | 860 |
| 8 | No. 30 | 830 |
| 9 | No. 34 | 790 |
| 10 | No. 37 | 810 |

It is apparent that each of the stabilizers in accordance with the invention is far superior to the Controls, which are conventional ultraviolet light stabilizers for polyvinyl chloride.

EXAMPLES 11 to 20

Polypropylene compositions were prepared using stabilizers of the invention and two of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table II | 0.3 |

The compositions were thoroughly blended in a Brabender Plastograph, and then compression-molded to form sheets 0.3 mm thick. Pieces 2.5 cm square were cut off from the sheets and exposed to a high voltage mercury lamp and with and without immersion in hot water at 80° C. for fifteen hours. The hours to failure were noted in comparison with two prior art stabilizers, bis(2,2,6,6-tetramethyl-4-piperidinyl)sebacate and oxabis(9-aza-3-hydroxymethyl-8,8,10,10-tetramethyl-1,5-dioxaspiro[5,5]-3-undecylmethane), and are shown in Table II.

TABLE II

| | | Hours to Failure | |
|---|---|---|---|
| Example No. | Stabilizer | Without Immersion | After Immersion for 15 hours |
| Control 1 | Bis (2,2,6,6-tetramethyl-4-piperidinyl) sebacate | 490 | 340 |
| 11 | No. 2 | 760 | 680 |
| 12 | No. 6 | 770 | 690 |
| 13 | No. 8 | 820 | 720 |
| 14 | No. 11 | 840 | 750 |
| 15 | No. 13 | 790 | 700 |
| 16 | No. 19 | 730 | 640 |
| 17 | No. 23 | 740 | 650 |
| 18 | No. 28 | 780 | 680 |
| 19 | No. 31 | 800 | 710 |
| 20 | No. 32 | 770 | 680 |

It is apparent from the above results that the compounds of the invention are superior stabilizers in enhancing the resistance of the polypropylene polymer composition to deterioration in the presence of ultraviolet light.

EXAMPLES 21 to 30

Ethylene-vinyl acetate copolymer compositions were prepared using stabilizers of the invention and two of the prior art, and having the following formulation:

| Ingredient | Parts by Weight |
|---|---|
| Ethylene-vinyl acetate copolymer | 100 |
| 2,6-di-t-butyl-p-cresol | 0.1 |
| Ca stearate | 0.1 |
| Zn stearate | 0.1 |
| Diisodecylphenylphosphite | 0.2 |
| Stabilizer as shown in Table III | 0.3 |

The stabilizer was blended with the polymer on a two-roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results in comparison with the two controls, tris(9-aza-3-ethyl-8,8,10,10-tetramethyl-1,5-dioxaspiro[5,5]-3-undecylmethyl)phosphite and 2-hydroxy-4-methoxybenzophenone, are given in Table III as percent retention of the initially determined tensile strength:

TABLE III

| Example No. | Stabilizer | % Retention of Tensile Strength After 500 hours |
|---|---|---|
| Control 1 | 2-Hydroxy-4-methoxybenzophenone | 68 |
| 21 | No. 3 | 76 |
| 22 | No. 5 | 80 |
| 23 | No. 9 | 83 |
| 24 | No. 15 | 79 |
| 25 | No. 18 | 77 |
| 26 | No. 21 | 77 |
| 27 | No. 25 | 76 |
| 28 | No. 26 | 79 |
| 29 | No. 29 | 81 |
| 30 | No. 32 | 82 |

It is apparent from the results that the stabilizer compositions in accordance with the invention are superior to the control in enhancing the resistance of the ethylene-vinyl acetate copolymer to deterioration in the presence of ultraviolet light.

EXAMPLES 31 to 40

High density polyethylene compositions were prepared using the stabilizers of the invention and two of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl)propionate)methane | 0.1 |
| Distearylthiodipropionate | 0.3 |
| Stabilizer as shown in Table IV | 0.3 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV.

TABLE IV

| Example No. | Stabilizer | Hours to Failure |
|---|---|---|
| Control 1 | Bis (2,2,6,6-tetramethyl-4-piperidinyl) adipate | 680 |
| 31 | No. 2 | 1,150 |
| 32 | No. 4 | 1,020 |
| 33 | No. 8 | 1,250 |
| 34 | No. 12 | 1,200 |
| 35 | No. 16 | 1,020 |
| 36 | No. 22 | 1,070 |
| 37 | No. 24 | 1,040 |
| 38 | No. 28 | 1,130 |
| 39 | No. 33 | 1,180 |
| 40 | No. 36 | 1,070 |

The stabilizers of the invention are clearly superior to the control in enhancing resistance of the polyethylene to degradation under ultraviolet light.

EXAMPLES 41 to 48

Acrylonitrile-butadiene-styrene terpolymer resin compositions were prepared using stabilizers of the invention and two of the prior art, and having the following formulation:

| Ingredient | Parts by Weight |
|---|---|
| Acrylonitrile-butadiene-styrene terpolymer | 100 |
| 4,4'-butylidene-bis-(2-tert-butyl-m-cresol) | 0.1 |
| Stabilizer as shown on Table V | 0.3 |

The stabilizer was blended with the resin on a two-roll mill, and sheets 3 mm thick were prepared by compression-molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| Example No. | Stabilizer | % Tensile Strength Retained |
|---|---|---|
| Control 1 | Bis(9-aza-3-ethyl-8,8,10,10-tetramethyl-1,5-dioxaspiro[5,5]-3-undecylmethyl) carbonate | 61 |
| Control 2 | 2(2'-hydroxy-5'-methylphenyl)benzotriazole | 63 |
| 41 | No. 6 | 86 |
| 42 | No. 9 | 89 |
| 43 | No. 11 | 90 |
| 44 | No. 17 | 83 |
| 45 | No. 20 | 85 |
| 46 | No. 26 | 86 |
| 47 | No. 30 | 87 |
| 48 | No. 35 | 82 |

It is apparent from the data that the stabilizers of the invention are superior to the Controls of the prior art.

EXAMPLES 49 to 55

Polyurethane resin compositions were prepared using stabilizers of the invention and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6-di-t-butyl-p-cresol | 0.1 |
| Stabilizer as shown in Table VI | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut out from the sheets, and exposed to ultraviolet light in a Weather-O-Meter for thirty hours. At the conclusion of the test period, tensile strength before and after exposure was determined, and the percent tensile strength retained after the exposure is given in Table VI.

TABLE VI

| Example No. | Stabilizer | % Retention of Tensile Strength |
|---|---|---|
| Control 1 | Bis(9-aza-3-ethyl-8,8,10,10-tetramethyl-1,5-dioxaspiro[5,5]-3-undecylmethyl)adipate | 58 |
| Control 2 | Bis(2,2,6,6-tetramethyl-4-piperidinyl)-1,6-hexamethylene dicarbamate | 55 |
| 49 | No. 4 | 72 |
| 50 | No. 11 | 78 |
| 51 | No. 18 | 77 |
| 52 | No. 23 | 75 |
| 53 | No. 27 | 75 |
| 54 | No. 31 | 78 |
| 55 | No. 37 | 74 |

The stabilizers of the invention are clearly superior to the controls in enhancing resistance of the polyurethane resin to degradation under ultraviolet light.

EXAMPLES 56 to 62

Conventional heat stabilizers for polymeric materials may lose their effectiveness because of volatilization or decomposition at high polymer processing temperatures. This is not true of the stabilizers of the invention, as shown by observing the effect of heat in repeated extrusions of ethylene-propylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-$\beta$-(3,5-di-t-butyl-4-hydroxyphenyl)propionate | 0.1 |
| Dilauryl thiodipropionate | 0.2 |
| Stabilizer as shown in Table VII | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure noted as shown in Table VII. The surface of the test pieces was also noted after exposure for 300 hours.

TABLE VII

| Example No. | Stabilizer | Hours to Failure Extruded 1 time | Extruded 5 times | Surface of test pieces after exposure for 500 hours |
|---|---|---|---|---|
| Control 1 | Bis(9-aza-8,8,10,10-tetramethyl-3-ethyl-1,5-dioxa-spiro[5,5]-3-un-decylmethyl)adipate | 400 | 260 | Bloom |
| 56 | No. 8 | 630 | 570 | No change |
| 57 | No. 10 | 660 | 610 | No change |
| 58 | No. 12 | 620 | 570 | No change |
| 59 | No. 13 | 590 | 520 | No change |
| 60 | No. 29 | 650 | 580 | No change |
| 61 | No. 32 | 570 | 500 | No change |
| 62 | No. 36 | 560 | 490 | No change |

The results show that substantial amounts of the Control stabilizer are lost by volatilization, after five extrusions, while the stabilizers of the invention are substantially retained in the polymer composition.

Having regard to the foregoing disclosure, the following is claimed as inventive and patentable embodiments thereof:

1. A 2,2,6,6-tetraalkyl-4-piperidyl-bis-spiro-ether useful as a stabilizer for lessening deterioration due to exposure to light of organic polymeric materials, having the formula:

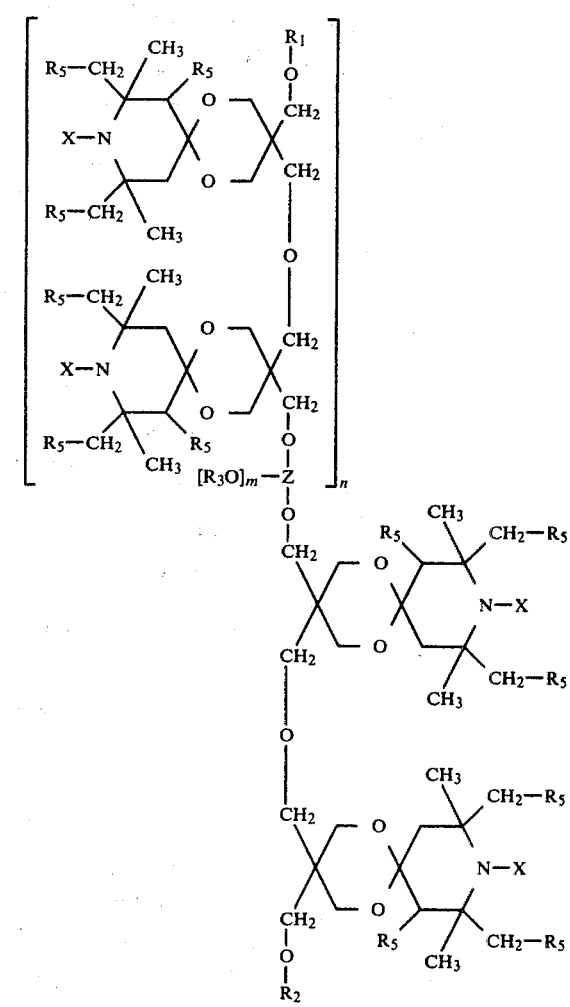

wherein:

$R_1$ and $R_2$ each are selected from the group consisting of hydrogen, alkyl, hydroxyalkyl, acyl, aryl, alkaryl, carbamoyl and ester having one to about twenty carbon atoms;

Z is selected from the group consisting of alkylene; arylene; alkylene-arylene;

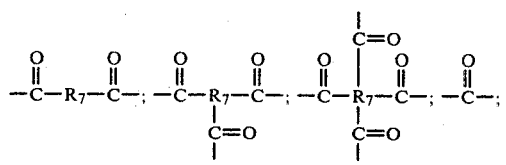

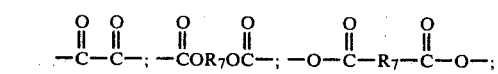

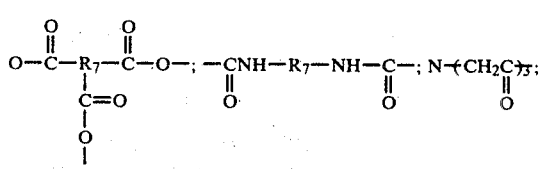

-continued $$-\underset{O}{\underset{\|}{C}}-NH-R_7-NH-\underset{O}{\underset{\|}{C}}-; \quad -\underset{\underset{C=O}{\underset{|}{NH}}}{\overset{|}{P}}-; \quad O=\overset{|}{\underset{|}{P}}-; \quad R_6-\overset{|}{\underset{|}{P}}-;$$

$$R_6-\overset{|}{\underset{|}{P}}=O; \quad -B-; \quad \underset{\underset{R_6}{\underset{|}{Si}}}{R_6}; \quad -\overset{|}{\underset{O}{\underset{|}{P}}}-O-R_7-O-\overset{|}{\underset{O}{\underset{|}{P}}}-;$$

[cyclic bis-phosphite structure with two P atoms each bonded to two O-C-C-O groups]

$R_6$ being alkyl or aryl and $R_7$ being alkylene, cycloalkylene or arylene, each having from one to about twenty carbon atoms;

$R_3$ is selected from the group consisting of alkyl and aryl having from one to about eighteen carbon atoms; and

[Structural formula showing two piperidine-like rings each with X—N, R5—CH2 and CH3 substituents, connected through spiro dioxane units containing R1—O—CH2 groups]

$R_5$ is selected from the group consisting of hydrogen and lower alkyl;

X is selected from the group consisting of hydrogen, oxyl (O·) and lower alkyl having from one to about five carbon atoms;

m is zero, one or two; and n is a number from one to ten.

2. A compound according to claim 1 in which m and n are each one.

3. A compound according to claim 1 in which n is zero.

4. A compound according to claim 1 in which $R_1$, $R_5$ and X are each hydrogen.

5. A compound according to claim 1 in which $R_5$ is lower alkyl having one or two carbon atoms, and $R_1$, and X are each hydrogen.

6. A compound according to claim 1 in which X is lower alkyl having one or two carbon atoms.

7. A compound according to claim 1 in which X is O·.

8. A compound according to claim 1 in which Z is alkylene.

9. A compound according to claim 1 in which Z is carbonyl C=O.

10. A compound according to claim 1 in which Z is $$-\overset{|}{\underset{|}{P}}-.$$

11. A compound according to claim 1 in which Z is $$-\underset{O}{\underset{\|}{C}}-R_7-\underset{O}{\underset{\|}{C}}-.$$

12. A compound according to claim 1 in which Z is $$-\underset{O}{\underset{\|}{C}}NHR_7NH\underset{O}{\underset{\|}{C}}-.$$

13. A compound according to claim 1 having the formula:

[Bracketed bis-piperidine structure with H—N groups, CH3 substituents, linked through spiro dioxane units with CH2—O—C=O termini, subscript 2]

[Additional structural formula showing piperidine rings with N—H and CH3 groups connected via CH2—O linkages and a central OH-bearing carbon]

14. A compound according to claim 1 having the formula:

15. A compound according to claim 1 having the formula:
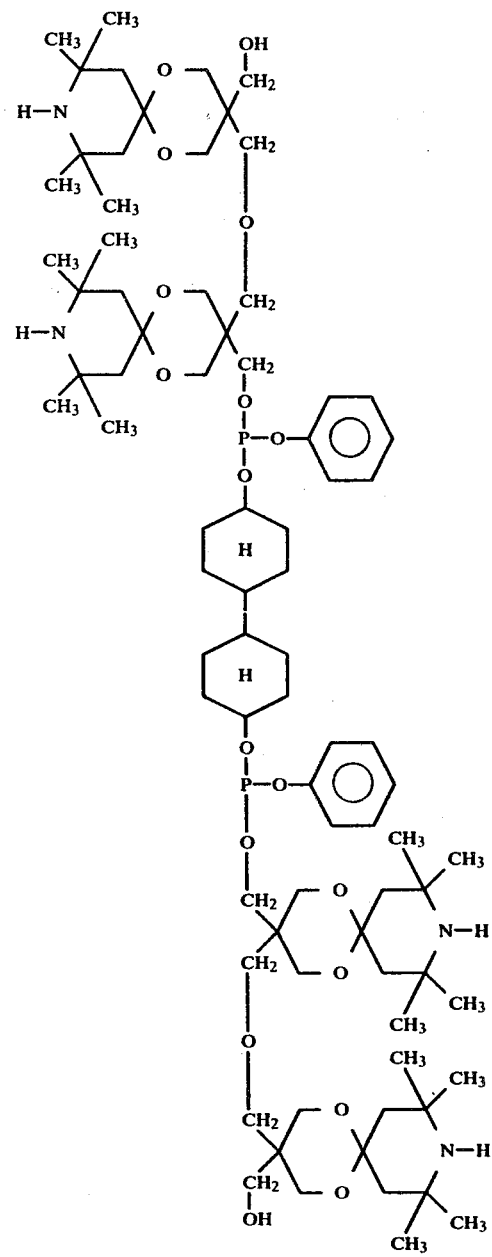
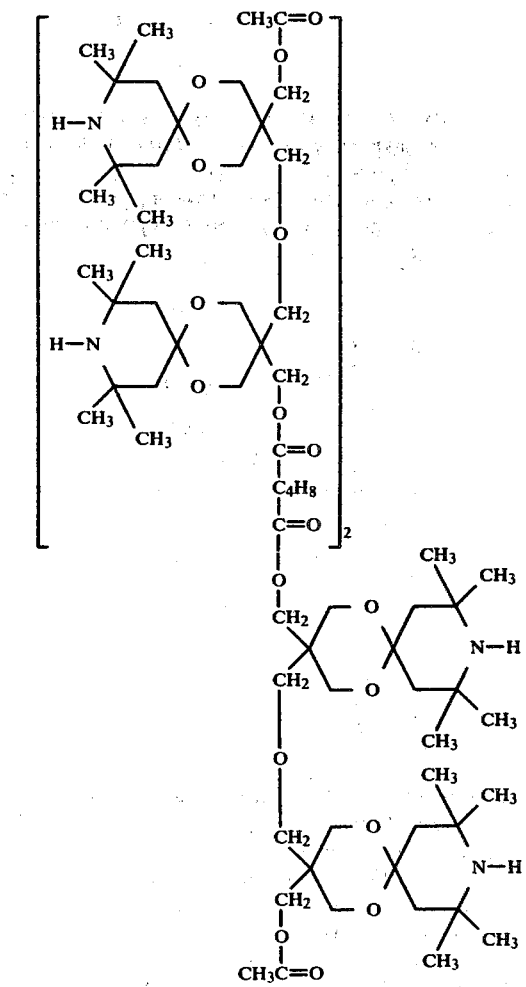
16. A compound according to claim 1 having the formula:

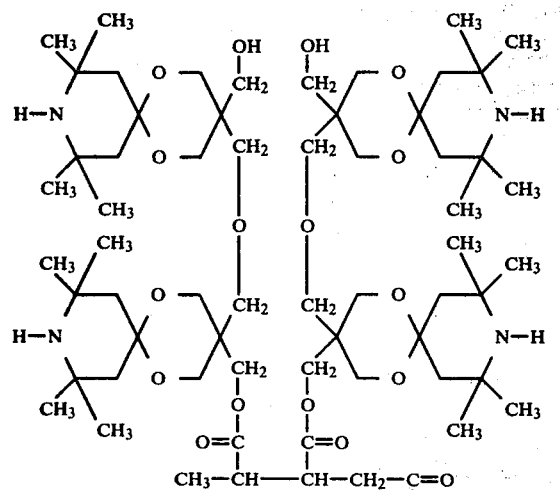
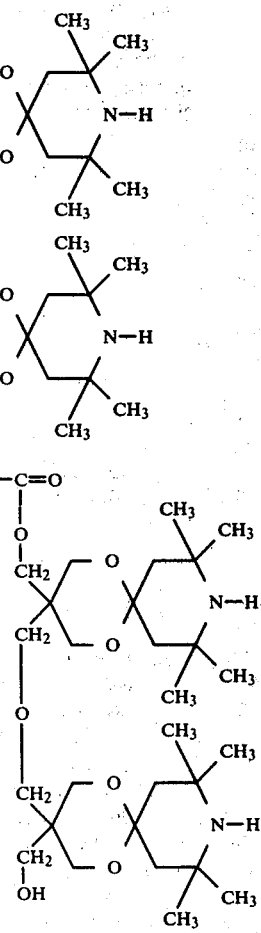
17. A compound according to claim 1 having the formula:
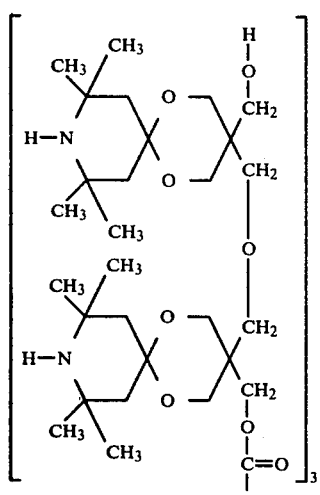
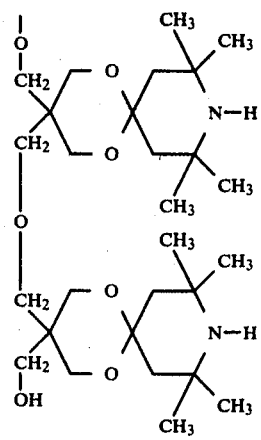
18. A polyvinyl chloride resin composition having improved resistance to deterioration when heated at 350° F., comprising a polyvinyl chloride resin formed at least in part of the recurring group:

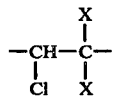

and having a chlorine content in excess of 49%, where X is either hydrogen or chlorine, and an amount sufficient to improve resistance to deterioration of the resin of a compound in accordance with claim 1.

19. A polyvinyl chloride resin composition in accordance with claim 18 in which the polyvinyl chloride resin is polyvinyl chloride homopolymer.

20. A polyvinyl chloride resin composition in accordance with claim 18 in which the polyvinyl chloride resin is a copolymer of vinyl chloride and vinyl acetate.

21. An olefin polymer composition having improved resistance to deterioration comprising an olefin polymer selected from the group consisting of polymers of alpha-olefins having from two to six carbon atoms and polystyrene, and an amount sufficient to improve resistance to deterioration of the resin of a compound in accordance with claim 1.

22. An olefin polymer composition in accordance with claim 21 wherein the polyolefin is polypropylene.

23. An olefin polymer composition in accordance with claim 21 wherein the polyolefin is polyethylene.

24. An olefin polymer composition in accordance with claim 21 wherein the polyolefin is ethylene-propylene copolymer.

25. An acrylonitrile-butadiene-styrene polymer having improved resistance to deterioration when heated at 300° F. comprising an acrylonitrile-butadiene-styrene polymer and an amount sufficient to improve resistance to deterioration of the resin of a compound in accordance with claim 1.

26. A polyurethane resin composition having improved resistance to deterioration comprising a polyurethane resin and an amount sufficient to improve resistance to deterioration of the resin of a compound in accordance with claim 1.

27. A 2,2,6,6-tetraalkyl-4-piperidyl-bis-spiro-ether useful as a stabilizer for lessening deterioration due to exposure to light of organic polymeric materials, having the formula:

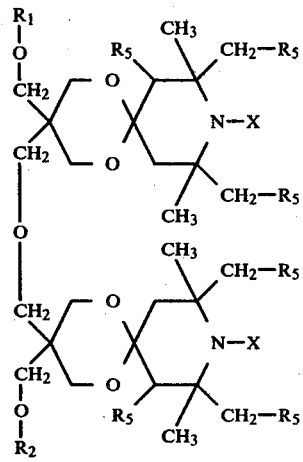

wherein:
$R_1$ is selected from the group consisting of hydrogen, alkyl, hydroxyalkyl, acyl, aryl, alkaryl, carbamoyl and ester having one to about twenty carbon atoms;

$R_2$ is selected from the group consisting of alkyl, hydroxyalkyl, acyl, aryl, alkaryl, carbamoyl and ester having one to about twenty carbon atoms;

$R_5$ is selected from the group consisting of hydrogen and lower alkyl;

X is selected from the group consisting of hydrogen, oxyl (O°) and lower alkyl having from one to about five carbon atoms.

* * * * *